US012788422B2

(12) United States Patent
Geusen et al.

(10) Patent No.: US 12,788,422 B2
(45) Date of Patent: Nov. 10, 2026

(54) DRIVING HANDLE, APPARATUS AND METHOD FOR RECAPTURING AN IMPLANT

(71) Applicant: Silara Medtech Inc., Santa Rosa, CA (US)

(72) Inventors: Mark Geusen, Santa Rosa, CA (US); Carl Poppe, Santa Rosa, CA (US)

(73) Assignee: Silara Medtech Inc., Santa Rosa, CA (US)

( * ) Notice: Subject to any disclaimer, the term of this patent is extended or adjusted under 35 U.S.C. 154(b) by 527 days.

(21) Appl. No.: 18/448,063

(22) Filed: Aug. 10, 2023

(65) Prior Publication Data

US 2024/0074777 A1 Mar. 7, 2024

Related U.S. Application Data

(63) Continuation of application No. PCT/US2022/015759, filed on Feb. 9, 2022.

(Continued)

(51) Int. Cl.
*A61B 17/29* (2006.01)
*A61B 17/00* (2006.01)
*A61F 2/24* (2006.01)

(52) U.S. Cl.
CPC .... *A61B 17/2909* (2013.01); *A61B 17/00234* (2013.01); *A61B 2017/00238* (2013.01); *A61B 2017/2918* (2013.01)

(58) Field of Classification Search
CPC .......... A61B 17/2909; A61B 17/00234; A61B 2017/00238; A61B 2017/2918;

(Continued)

(56) References Cited

U.S. PATENT DOCUMENTS 4,444,402 A 4/1984 Esclue et al.
5,127,626 A 7/1992 Hilal et al.

(Continued)

FOREIGN PATENT DOCUMENTS

EP 2723274 A2 4/2014
JP 2012505048 A 3/2012

(Continued)

OTHER PUBLICATIONS

Rezaei et al.; A. Study on mechanical properties of UHMWPE/PET composites using robust design; Iranian Polymer Journal; 2006; 15(30); pp. 3-12; Oct. 2005.

(Continued)

*Primary Examiner* — Bruce E Snow
(74) *Attorney, Agent, or Firm* — Shay Glenn LLP

(57) ABSTRACT

The present disclosure provides a driving handle, an apparatus and a method for recapturing an implant. The driving handle for recapturing an implant comprises: a first slider and a second slider, the first slider and the second slider being distributed in a longitudinal direction; a fixing barrel which defines a tube passage that receives the first slider and the second slider; a movable barrel which sleeves on the fixing barrel; wherein the movable barrel is configured to move spirally along the fixing barrel during at least a portion of a stroke to drive the first slider and the second slider to move synchronously and linearly along the tube passage. The present disclosure can alleviate the technical problem of difficult recapturing operation due to relatively high resistance when recapturing the implant.

10 Claims, 10 Drawing Sheets

Related U.S. Application Data

(60) Provisional application No. 63/148,000, filed on Feb. 10, 2021.

(58) Field of Classification Search
CPC ............ A61F 2/2436; A61F 2002/9528; A61F 2002/9534; A61F 2/9517; A61F 2/2466
See application file for complete search history.

(56) References Cited

U.S. PATENT DOCUMENTS

| | | | |
|---|---|---|---|
| 5,593,424 A | 1/1997 | Northrup, III | |
| 5,868,779 A | 2/1999 | Ruiz | |
| 5,895,404 A | 4/1999 | Ruiz | |
| 5,928,261 A | 7/1999 | Ruiz | |
| 5,935,112 A | 8/1999 | Stevens et al. | |
| 5,954,765 A | 9/1999 | Ruiz | |
| 6,261,273 B1 | 7/2001 | Ruiz | |
| 6,702,826 B2 | 3/2004 | Liddicoat et al. | |
| 6,860,463 B2 | 3/2005 | Hartley | |
| 6,942,694 B2 | 9/2005 | Liddicoat et al. | |
| 6,986,775 B2 | 1/2006 | Morales et al. | |
| 7,166,127 B2 | 1/2007 | Spence et al. | |
| 7,297,150 B2 | 11/2007 | Cartledge et al. | |
| 7,338,518 B2 | 3/2008 | Chobotov | |
| 7,588,582 B2 | 9/2009 | Starksen et al. | |
| 7,753,924 B2 | 7/2010 | Starksen et al. | |
| 7,892,275 B2 | 2/2011 | Hartley et al. | |
| 8,202,315 B2 | 6/2012 | Hlavka et al. | |
| 8,241,351 B2 | 8/2012 | Cabiri | |
| 8,277,502 B2 | 10/2012 | Miller et al. | |
| 8,512,401 B2 | 8/2013 | Murrary et al. | |
| 8,518,107 B2 | 8/2013 | Tsukashima et al. | |
| 8,864,822 B2 | 10/2014 | Spence et al. | |
| 8,911,494 B2 | 12/2014 | Hammer et al. | |
| 8,926,697 B2 | 1/2015 | Gross et al. | |
| 8,945,059 B2 | 2/2015 | Loewen | |
| 9,011,520 B2 | 4/2015 | Miller et al. | |
| 9,180,005 B1 | 11/2015 | Lashinski et al. | |
| 9,192,471 B2 | 11/2015 | Bolling | |
| 9,216,277 B2 | 12/2015 | Myers | |
| 9,446,018 B2 | 9/2016 | Su et al. | |
| 9,492,276 B2 | 11/2016 | Lee et al. | |
| 9,526,522 B2 | 12/2016 | Wood et al. | |
| 9,713,530 B2 | 7/2017 | Cabiri et al. | |
| 9,895,222 B2 | 2/2018 | Zeng et al. | |
| 10,251,763 B2 | 4/2019 | Wang | |
| 10,463,483 B2 | 11/2019 | Lim et al. | |
| 10,687,932 B2 | 6/2020 | Zi et al. | |
| 10,758,729 B2 | 9/2020 | McDonnell et al. | |
| 10,894,162 B2 | 1/2021 | Soltis et al. | |
| 11,571,301 B2 | 2/2023 | Yellin et al. | |
| 11,672,661 B2 | 6/2023 | Greenan et al. | |
| 12,053,597 B2 * | 8/2024 | Zhou | A61F 2/2436 |
| 12,138,168 B2 | 11/2024 | Calibri et al. | |
| 2003/0225379 A1 | 12/2003 | Schaffer et al. | |
| 2004/0049207 A1 | 3/2004 | Goldfarb | |
| 2004/0088047 A1 | 5/2004 | Spence et al. | |
| 2004/0267313 A1 | 12/2004 | Amery et al. | |
| 2005/0070820 A1 | 3/2005 | Boutillette et al. | |
| 2006/0020336 A1 | 1/2006 | Liddicoat | |
| 2006/0025855 A1 | 2/2006 | Lashinski et al. | |
| 2007/0049942 A1 | 3/2007 | Hindrichs et al. | |
| 2007/0161969 A1 | 7/2007 | Anderson | |
| 2007/0276461 A1 | 11/2007 | Andreas et al. | |
| 2008/0294177 A1 | 11/2008 | To et al. | |
| 2009/0088836 A1 | 4/2009 | Bishop et al. | |
| 2009/0093670 A1 | 4/2009 | Annest et al. | |
| 2010/0107719 A1 | 5/2010 | Geho | |
| 2010/0280607 A1 | 11/2010 | Milo | |
| 2011/0082538 A1 | 4/2011 | Dahlgren et al. | |
| 2011/0144592 A1 | 6/2011 | Wong et al. | |
| 2011/0166649 A1 | 7/2011 | Gross et al. | |
| 2012/0143323 A1 | 6/2012 | Hasenkam et al. | |
| 2012/0245604 A1 | 9/2012 | Tegzes | |
| 2012/0296407 A1 | 11/2012 | Caselnova | |
| 2013/0123841 A1 | 5/2013 | Lyon | |
| 2013/0190863 A1 | 7/2013 | Call et al. | |
| 2014/0052232 A1 | 2/2014 | Cragg et al. | |
| 2015/0018941 A1 | 1/2015 | Lee et al. | |
| 2016/0030175 A1 | 2/2016 | Madjarov et al. | |
| 2016/0045311 A1 | 2/2016 | McCann et al. | |
| 2016/0120645 A1 | 5/2016 | Alon | |
| 2016/0213919 A1 | 7/2016 | Suwito et al. | |
| 2016/0317302 A1 | 11/2016 | Madjarov et al. | |
| 2016/0338829 A1 | 11/2016 | Call et al. | |
| 2017/0056171 A1 | 3/2017 | Cooper et al. | |
| 2017/0097046 A1 | 4/2017 | Hadden | |
| 2017/0165068 A1 | 6/2017 | Machold et al. | |
| 2017/0189187 A1 | 7/2017 | Ruiz et al. | |
| 2017/0340443 A1 | 11/2017 | Sterns et al. | |
| 2018/0000619 A1 | 1/2018 | Longo et al. | |
| 2018/0140445 A1 | 5/2018 | Geusen | |
| 2018/0256334 A1 | 9/2018 | Sheps et al. | |
| 2018/0311039 A1 * | 11/2018 | Cohen | A61F 2/2418 |
| 2018/0318080 A1 | 11/2018 | Quill et al. | |
| 2019/0125325 A1 | 5/2019 | Sheps et al. | |
| 2019/0240020 A1 | 8/2019 | Rafiee et al. | |
| 2019/0269445 A1 | 9/2019 | Singh et al. | |
| 2019/0321205 A1 | 10/2019 | Schmitt et al. | |
| 2020/0015970 A1 | 1/2020 | Solem et al. | |
| 2020/0072381 A1 | 3/2020 | Turnau et al. | |
| 2020/0188092 A1 | 6/2020 | Metcalf et al. | |
| 2020/0188108 A1 | 6/2020 | Grimm et al. | |
| 2020/0188111 A1 | 6/2020 | Metcalf et al. | |
| 2020/0230371 A1 | 7/2020 | Klausen et al. | |
| 2020/0246143 A1 * | 8/2020 | Ekvall | A61F 2/95 |
| 2021/0015478 A1 | 1/2021 | Sampson et al. | |
| 2021/0030540 A1 | 2/2021 | Marchand et al. | |
| 2021/0052387 A1 | 2/2021 | Greenan et al. | |
| 2021/0128302 A1 | 5/2021 | Solem et al. | |
| 2021/0220138 A1 | 7/2021 | Edminston et al. | |
| 2021/0228349 A1 | 7/2021 | Vidlund et al. | |
| 2021/0275306 A1 | 9/2021 | Greenan et al. | |
| 2022/0054270 A1 | 2/2022 | Manash et al. | |
| 2022/0079749 A1 | 3/2022 | Patel et al. | |
| 2022/0079762 A1 | 3/2022 | Serina et al. | |
| 2023/0107129 A1 | 4/2023 | Mohl | |
| 2023/0120494 A1 | 4/2023 | Mohl et al. | |
| 2024/0074777 A1 * | 3/2024 | Geusen | A61B 17/00234 |
| 2024/0341957 A1 | 10/2024 | Khairkhahan et al. | |
| 2025/0090324 A1 | 3/2025 | Greenan et al. | |

FOREIGN PATENT DOCUMENTS

| | | |
|---|---|---|
| JP | 2019536576 A | 12/2019 |
| WO | WO2008/112740 A2 | 9/2008 |
| WO | WO2009/052438 A2 | 4/2009 |
| WO | WO2013/155970 A1 | 10/2013 |
| WO | WO2016/150260 A1 | 9/2016 |
| WO | WO2016/150261 A1 | 9/2016 |
| WO | WO2019/105073 A1 | 6/2019 |
| WO | WO2019/116322 A1 | 6/2019 |
| WO | WO2019/179447 A1 | 9/2019 |
| WO | WO2020/011880 A1 | 1/2020 |
| WO | WO2020/134052 A1 | 7/2020 |
| WO | WO2020/134053 A1 | 7/2020 |
| WO | WO2021/034789 A1 | 2/2021 |
| WO | WO2022/055923 A1 | 3/2022 |
| WO | WO2022/066525 A2 | 3/2022 |
| WO | WO2022/086769 A1 | 4/2022 |
| WO | WO2022/090907 A1 | 5/2022 |
| WO | WO2022/115677 A1 | 6/2022 |
| WO | WO2022/173790 A1 | 8/2022 |
| WO | WO2022/261266 A1 | 12/2022 |

OTHER PUBLICATIONS

Greenan et al.; U.S. Appl. No. 18/884,022 emtitled "Hemostasis and flushing method and apparatus for trans-catheter annuloplasty," Sep. 12, 2024.

* cited by examiner

DRIVING HANDLE, APPARATUS AND METHOD FOR RECAPTURING AN IMPLANT

CLAIM OF PRIORITY

The present disclosure is a continuation application of International Application No. PCT/US2022/015759, filed Feb. 9, 2022, entitled "DRIVING HANDLE, APPARATUS AND METHOD FOR RECAPTURING AN IMPLANT", which claims the benefit of U.S. Provisional Application No. 63/148,000, filed on Feb. 10, 2021, entitled "DRIVING HANDLE, APPARATUS AND METHOD FOR RECAPTURING AN IMPLANT", the entire disclosures of which are incorporated herein by reference for all purposes.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The present disclosure relates to the field of medical instruments, in particular to a driving handle, an apparatus and a method for recapturing an implant.

BACKGROUND

For patients with high-risk heart valve diseases, a heart valve prosthesis is implanted into a native valve site through a catheter, and the newly-implanted valve prosthesis replaces the native valve to perform a physiological function after it is completely released, which is an effective means to treat the heart valve diseases.

The heart valve prosthesis is one of the implants. In the event that the implant is improperly sized during surgery or the implant is damaged during implantation, resulting in the implant becoming unsuitable for the patient's physiological anatomy, the medical staff need to take the implants out of the human body and re-implant new implants.

In order to recapture the implant, it is generally necessary to use a recapturing apparatus, which usually comprises a recapturing tube, a sheath tube and a handle. A recapturing net for capturing the implant is connected to a distal end of the recapturing tube, and the sheath tube sleeves outside the recapturing tube, and both the sheath tube and the recapturing tube are connected with the handle. Firstly, the distal end of the recapturing tube and the recapturing net are moved to the outside of the sheath tube by operating the handle to move the sheath tube and recapturing tube; then, the recapturing net is unfolded to capture the implant to be recaptured. After the recapturing net has captured the implant, the recapturing net wraps around the implant. The implant can also be pulled into the sheath tube together with the recapturing tube by operating the handle. When the recapturing net enters the sheath tube, it is gradually reduced by the constraint of the sheath tube, so that it is convenient to recapture the implant.

As shown in FIG. 1, an introducer 16 is typically provided during the procedure for guiding the delivery of the implant. The introducer 16 has a sheath tube, referred to as a catheter sheath 15 for forming a blood vessel channel, and the sheath tube 11 and the recapturing tube 12 of the recapturing apparatus penetrate through the catheter sheath 15.

When recapturing larger implants, such as larger-sized heart valve prostheses, there is a problem in that it is difficult to accommodate the implant due to the smaller inner diameter of the sheath tube. In this case, since the inner diameter of the catheter sheath is larger than that of the sheath tube, the recapturing tube and the sheath tube can be pulled proximally after the expanded recapturing net captures the heart valve prosthesis to be recaptured, and simultaneously a delivery device (e.g., a positioning guide wire) connected to the heart valve prosthesis is pulled, to pull the recapturing net and the heart valve prosthesis directly into the catheter sheath. The recapturing net is gradually reduced by the constraint of the catheter sheath as it enters the catheter sheath. The heart valve prosthesis is wrapped tightly and pulled into the catheter sheath until the recapturing tube and heart valve prosthesis are pulled out of the body.

However, when the recapturing net that has captured the heart valve prosthesis is drawn into the catheter sheath, the resistance is relatively large, and the pulling force that needs to be applied to the recapturing tube and the sheath tube is relatively high.

SUMMARY OF THE DISCLOSURE

An object of the present disclosure is to provide a driving handle for recapturing an implant, a recapturing apparatus including the driving handle and a recapturing method of recapturing an implant by using the recapturing apparatus, so as to alleviate the technical problem of difficult recapturing operation due to relatively high resistance when recapturing the implant.

The present disclosure provides a driving handle for recapturing an implant that may include a first slider, a second slider, a fixing barrel, and a movable barrel. The first slider and the second slider are distributed in a longitudinal direction. The fixing barrel defines a tube passage that receives the first slider and the second slider. The movable barrel sleeves on the fixing barrel. Wherein the movable barrel is configured to move spirally along the fixing barrel during at least a portion of a stroke to drive the first slider and the second slider to move synchronously and linearly along the tube passage. Alternatively, the movable barrel may move spirally along the fixing barrel over the entire stroke. Alternatively, the movable barrel may move linearly along the fixing barrel during a portion of the stroke and move spirally along the fixing barrel during another portion of the stroke.

Alternatively, the fixing barrel is provided with a first outer spiral groove, and the at least a portion of the stroke is defined by at least a portion of the first outer spiral groove. For example, the length of the first outer spiral groove may be set to correspond only to the stroke of the synchronous linear motion of the second slider and the first slider. As another example, the length of the first outer spiral groove may also be set to correspond to a partial stroke of the first slider before the first slider engages with the second slider as well as the stroke of synchronous linear motion of the first slider and the second slider. The movable barrel is connected with the first slider, and is provided with an inner protrusion. The inner protrusion is configured to be movable along the first outer spiral groove to guide spiral motion of the movable barrel. Preferably, the inner protrusion is configured as an inner spiral rib. Alternatively, the fixing barrel is provided with a first outer spiral groove, and the at least a portion of the stroke is defined by at least a portion of the first outer spiral groove. Preferably, the movable barrel is connected with the first slider. The movable barrel is provided with an inner protrusion. The spiral motion of the movable barrel causes the inner protrusion to move along the first outer spiral groove to produce the linear motion during the at least a portion of the stroke.

Alternatively, the movable barrel moves linearly along the fixing barrel during a portion of the stroke and move spirally along the fixing barrel during another portion of the stroke. For example, the outer wall of the fixing barrel is provided with a sliding cylindrical surface. The sliding cylindrical surface and the first outer spiral groove are sequentially distributed along the recapturing direction. The sliding cylindrical surface is adapted for the movement of the inner protrusion along the longitudinal direction. Preferably, the sliding cylindrical surface is provided with a longitudinal elongated rib extending in the longitudinal direction.

Alternatively, the movable barrel moves spirally along the fixing barrel over the entire stroke. For example, the outer wall of the fixing barrel is provided with a second outer spiral groove. The second outer spiral groove and the first outer spiral groove are sequentially distributed along the recapturing direction. The screw pitch of the second outer spiral groove is greater than that of the first outer spiral groove. Preferably, the inner protrusion is configured as a ball.

Preferably, the fixing barrel is provided with a first line-type groove extending in the longitudinal direction. The first slider is provided with a first slider bump extending to protrude out of the first line-type groove. The movable barrel is provided with an annular groove configured to receive the first slider bump and to allow the annular groove to be rotatable relative to the first slider bump. Alternatively, the second slider is provided with a second slider bump which extends to protrude out of the first line-type groove. In some embodiments, the movable barrel comprises a barrel body and a ring body fixedly connected to the inner side of the barrel body, and the inner protrusion is provided on the ring body.

Preferably, the first slider is a sheath tube piston, the second slider is a net piston, and the sheath tube piston and the net piston are sequentially distributed in the recapturing direction. The net piston is provided with a flexible member, and the side wall of the fixing barrel is provided with a limiting groove. The limiting groove is configured to be able to receive the flexible member to limit movement of the net piston relative to the fixing barrel in the recapturing direction. The sheath tube piston is connected with a sheath tube piston cap. The sheath tube piston cap is provided at one end of the sheath tube piston that is close to the net piston. The sheath tube piston cap is configured to be suitable for disengaging the flexible member from the limiting groove to release the limitation.

Preferably, the inner wall of the fixing barrel is provided with a limiting step, and the limiting step can limit the movement of the net piston in the reverse direction of the recapturing direction. In particular, the limiting step limits the movement of the net piston in the reverse direction of the recapturing direction when being abutted by the net piston.

The present disclosure provides another driving handle for recapturing an implant, the driving handle includes a first slider, a second slider, a first fixing barrel, a first movable barrel and a second movable barrel. The first slider and the second slider are distributed in a longitudinal direction. The first fixing barrel defines a tube passage that is configured to receive the first slider and the second slider. The first movable barrel and the second movable barrel sleeve outside the first fixing barrel at an interval. Wherein the first movable barrel is configured to rotatably move relative to the first fixing barrel in a first stroke stage to drive the first slider to move linearly, and the second movable barrel is configured to rotatably move relative to the first fixing barrel during at least a portion of a second stroke stage to drive the second slider and the first slider to move synchronously and linearly. For example, the entire stroke of the synchronous linear motion of the second slider and the first slider may be entirely produced by the driving of the second movable barrel, or one portion of the stroke of the synchronous linear motion is produced by the driving of the first movable barrel and the other portion of the stroke is produced by the driving of the second movable barrel.

Alternatively, the entire stroke of the synchronous linear motion of the second slider and the first slider may be entirely produced by the driving of the second movable barrel. Preferably, the first fixing barrel is provided with a second line-type groove in the longitudinal direction, the first slider is provided with a first outer protrusion, the second slider is provided with a second outer protrusion, the first outer protrusion and the second outer protrusion extend to protrude out of the second line-type groove. Preferably, the first movable barrel is provided with a first inner spiral groove, and the second movable barrel is provided with a second inner spiral groove. The rotational motion of the first movable barrel causes the first inner spiral groove to cooperate with the first outer protrusion to produce a linear motion during the first stroke stage. The rotational motion of the second movable barrel causes the second inner spiral groove to cooperate with the second outer protrusion to produce a synchronous linear motion during the second stroke stage. Preferably, the first outer protrusion is configured as a first outer spiral rib that cooperates with the first inner spiral groove, and the second outer protrusion is configured as a second outer spiral rib that cooperates with the second inner spiral groove. Preferably, the screw pitch of the second inner spiral groove is smaller than that of the first inner spiral groove.

Preferably, the first slider is provided with a longitudinal through hole and a rotatable locking ring, and a locking ring inner bump is provided on the inner side of the locking ring. Preferably, the second slider is provided with a second claw, and the second claw is adapted to pass through the longitudinal through hole during engagement of the first slider with the second slider. Preferably, a rotatable knob is arranged outside the first fixing barrel, and rotation of the knob causes the locking ring to rotate so that the locking ring inner bump engages the second claw. Alternatively, the first slider is provided with a first claw which is in rotatable engagement with the locking ring inner bump. Alternatively, an arc-shaped groove is provided on an inner side of the locking ring or an end surface of the locking ring close to the first slider. The first slider is provided with a convex portion adapted to the arc-shaped groove, and the convex portion is rotatably engaged with the arc-shaped groove.

Preferably, the first slider is a sheath tube piston and the second slider is a net piston. The handle further includes a second fixing barrel, and the second fixing barrel sleeves fixedly outside the first fixing barrel. A proximal end of the first movable barrel and a distal end of the second movable barrel are rotatably fixed between the first fixing barrel and the second fixing barrel. Preferably, the knob sleeves outside the second fixing barrel and is provided with a knob bump. The side wall of the second fixing barrel is provided with a knob through hole through which the knob bump passes. Preferably, the locking ring, the sheath tube piston and the net piston are all disposed within the first fixing barrel, and the first fixing barrel is provided with a third line-type groove extending in the longitudinal direction. A locking ring outer bump is provided on the outer side of the locking ring, and the locking ring outer bump extends to protrude out of the third line-type groove. The locking ring outer bump and the knob bump cooperate in a manner of a groove tenon to realize the engagement of the locking ring and the knob. Alternatively, the locking ring outer bump is provided with a protrusion, and a groove is arranged on the knob bump. Alternatively, the locking ring outer bump is provided with a groove, and a protrusion is arranged on the knob bump.

The present disclosure further provides an implant recapturing apparatus, comprising a recapturing net, a recapturing tube, a sheath tube and the driving handle for recapturing an implant as described above. Preferably, the recapturing tube and the sheath tube are slidably disposed within the tube passage. Preferably, the sheath tube sleeves outside the recapturing tube, and the distal end of the recapturing tube is connected with the recapturing net. Preferably, the proximal end of the sheath tube is connected with the first slider and the proximal end of the recapturing tube is connected with the second slider.

The present disclosure provides an implant recapturing method, comprising: providing an implant recapturing apparatus which includes a driving handle for recapturing an implant, a recapturing net, a recapturing tube and a sheath tube, the handle including a movable barrel; pulling or rotating the movable barrel to drive the sheath tube to move proximally, thereby releasing and unfolding the recapturing net at the distal end of the recapturing tube; and rotating the movable barrel to drive the recapturing tube, the recapturing net, the implant, and the sheath tube together to move proximally into the catheter sheath.

The present disclosure further provides an implant recapturing method, comprising: providing an implant recapturing apparatus which includes a driving handle for recapturing an implant, a recapturing net, a recapturing tube and a sheath tube, the handle including a first movable barrel and a second movable barrel; rotating the first movable barrel to drive the sheath tube to move proximally, thereby releasing and unfolding the recapturing net at the distal end of the recapturing tube; and rotating the second movable barrel to drive the recapturing tube, the recapturing net, the implant, and the sheath tube together to move proximally into the catheter sheath.

The present disclosure has the following features and advantages:

- the handle is capable of converting the rotation of the movable barrel into a linear movement of the second slider, facilitating the operator to apply a large longitudinal force to the second slider, thereby driving the second slider and a catheter element connected to the second slider to move in the recapturing direction to smoothly pull the respective catheter element and the captured implant of the recapturing apparatus into the catheter sheath. Since the rotation operation is more convenient than the pulling operation, the present disclosure can reduce the difficulty of the recapturing operation, and solve the problem of the difficulty in the recapturing operation due to the large resistance when recapturing the implant.

BRIEF DESCRIPTION OF THE DRAWINGS

In order to more clearly explain the technical solution in the embodiments of the present disclosure, drawings that need to be used in description of the embodiments will be simply introduced below. Obviously the drawings in the following description are merely some examples of the present disclosure. For persons ordinarily skilled in the art, it is also possible to obtain other drawings according to these drawings without making creative efforts.

REFERENCE SIGNS

Figure 1:
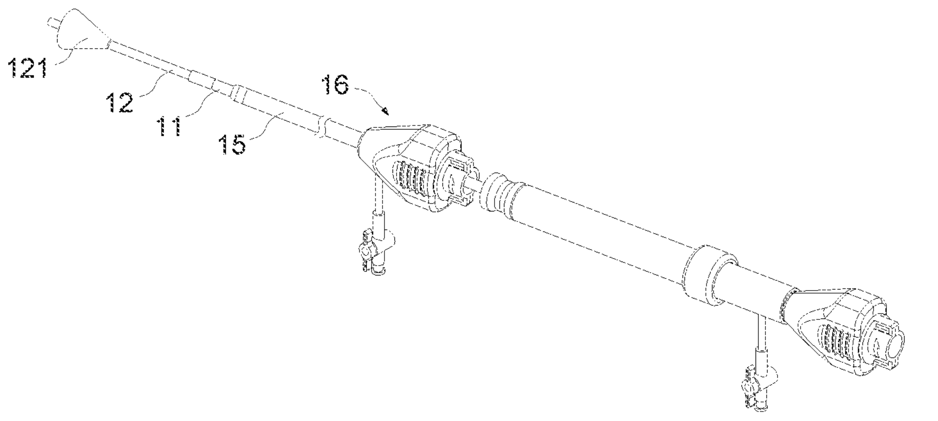
FIG. 1 is an assembling diagram of a sheath tube, a recapturing tube and a catheter sheath in the prior art.

11: sheath tube; 12: recapturing tube; 121: recapturing net; 131: inner tube; 132: hemostatic valve device; 14: development marker; 15: catheter sheath; 16: introducer;

20: fixing barrel; 201: tube passage; 202: third sub-barrel body; 203: fourth sub-barrel body; 200: recapturing direction;

231: grip; 232: fixing handle cap; 233: flush tube; 2331: flush valve; 234: prompt sign;

24: first line-type groove; 251: sliding cylindrical surface; 252: longitudinal elongated rib; 26: second outer spiral groove; 27: limiting step;

28: first fixing barrel; 281: second line-type groove; 282: third line-type groove; 283: fixing post;

29: second fixing barrel; 291: knob through hole; 292: fixing hole; 293: spacer; 294: positioning teeth;

30: movable barrel/second movable barrel; 31: annular groove; 32: barrel body; 321: first sub-barrel body; 322: second sub-barrel body; 331: first ring body; 332: second ring body; 341: connecting groove; 342: connecting bump;

40: first movable barrel; 41: first inner spiral groove; 42: first outer protrusion/first outer spiral rib; 43 positioning groove;

511: second inner spiral groove; 512: second outer protrusion/second outer spiral rib;

521: first outer spiral groove; 522: inner protrusion; 523: inner spiral rib; 524: ball;
60: net piston/second slider; 61: second slider bump; 62: net piston cap; 63: flexible member; 631: limiting groove;
70: sheath tube piston/first slider; 71: first slider bump; 72: sheath tube piston cap; 73: sealing ring; 74: longitudinal through hole;
811: second claw; 812: first claw; 82: knob; 821 knob bump; 83: locking ring; 831: locking ring inner bump; 832: locking ring outer bump.

DETAILED DESCRIPTION

Hereinafter the technical solution in the embodiments of the present disclosure will be described clearly and completely in combination with the accompanying drawings in the embodiments of the present disclosure, and obviously the described embodiments are merely part of the embodiments, not all of the embodiments. Any other embodiment obtained by those skilled in the art based on the embodiments of the present disclosure without paying any creative labor fall within the protection scope of the present disclosure.

Driving Handle for Recapturing an Implant in the First Embodiment

With reference to a driving handle for recapturing an implant shown in FIGS. 2A-2C, 7A and 7B, the handle may include a first slider 70, a second slider 60, a fixing barrel 20 and a movable barrel 30. The fixing barrel 20 defines a tube passage 201, and the first slider 70 and the second slider 60 are distributed longitudinally in the tube passage 201. The tube passage 201 is configured to receive the first slider 70 and the second slider 60. The movable barrel 30 sleeves on the fixing barrel 20. The movable barrel 30 is configured to move spirally along the fixing barrel 20 during at least a portion of the stroke to drive the first slider 70 and the second slider 60 to move synchronously and linearly along the tube passage 201.

The driving handle for recapturing an implant is applied to the surgery of recapturing the implant via a catheter. The first slider 70 acts as a sheath tube piston and the second slider 60 acts as the net piston. The sheath tube 11 sleeves outside the recapturing tube 12, and the proximal end of the recapturing tube 12 extends beyond the proximal end of the sheath tube 11. The sheath tube 11 and the recapturing tube 12 both pass through the tube passage 201 and are both movable within the tube passage 201. The sheath tube 11 is fixedly connected to a sheath tube piston, and the recapturing tube 12 is fixedly connected to the net piston. The recapturing tube 12 and the sheath tube 11 are capable of inserting from the proximal end of the fixing barrel 20, passing out from the distal end of the fixing barrel 20, and entering the blood vessel. The recapturing direction 200 is parallel to the longitudinal direction of the fixing barrel 20, in particular the direction in which the distal end of the fixing barrel 20 points towards the proximal end thereof. The proximal and distal ends are defined in a conventional manner of an implantation surgery, with the operator as the reference object, i.e. with the end close to the operator being the proximal end and the end remote from the operator being the distal end. The first slider 70 and the second slider 60 are sequentially distributed from distal to proximal along the recapturing direction 200.

In some embodiments, with reference to FIGS. 2A to 6D, the outer surface of the fixing barrel 20 close to the proximal end is provided with a first outer spiral groove 521, the inner wall of the movable barrel 30 is provided with an inner protrusion 522, and the inner protrusion 522 is configured to be guided for spiral motion by the first outer spiral groove 521. The movable barrel 30 is relatively rotatably coupled with the first slider 70. When the movable barrel 30 is rotated, the movable barrel 30 makes a spiral motion along the first outer spiral groove 521 together with the inner protrusion 522. The movable barrel 30 makes a spiral motion, i.e., the movable barrel 30 moves proximally in the longitudinal direction of the fixing barrel 20 while being rotated. The movable barrel 30 may deliver the movement in the longitudinal direction of the fixing barrel 20 to the first slider 70, move the first slider 70 into engagement with the second slider 60, in order to cause the second slider 60 to move proximally along the longitudinal direction of the fixing barrel 20 together with the movable barrel 30 after engaging with the first slider 70.

Figure 2A:
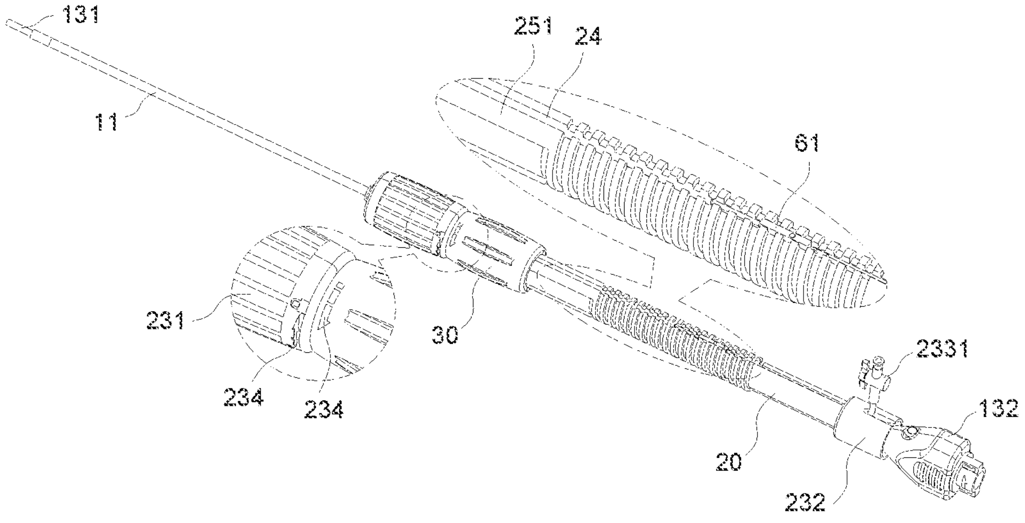
FIGS. 2A to 2C show schematic diagrams of a driving handle for recapturing an implant in the first embodiment provided in this disclosure.
Figure 2B:
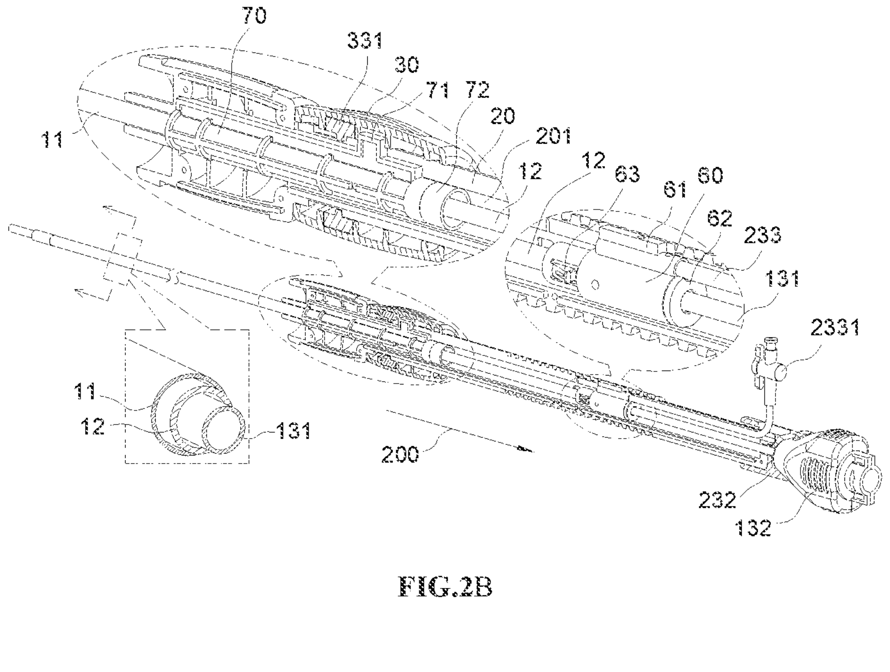
Figure 2C:
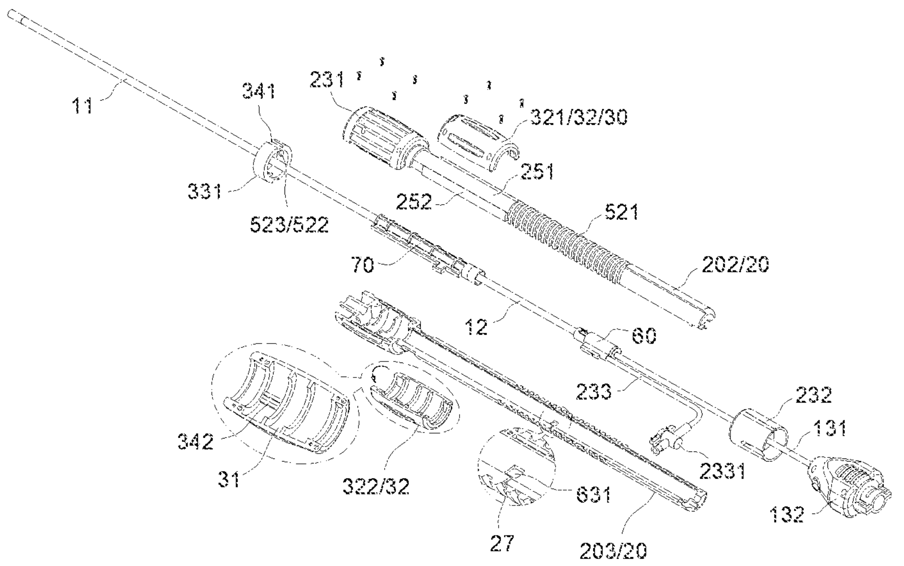

With reference to FIGS. 2A to 2C, the fixing barrel 20 is provided with a first line-type groove 24 extending in the longitudinal direction, and the first slider 70 is provided with a first slider bump 71. The first slider bump 71 extends in a radial direction of the fixing barrel 20 to protrude out of the first line-type groove 24, such that the first slider bump 71 is slidable in the first line-typed groove 24. The movable barrel 30 is provided with an annular groove 31 configured to receive the first slider bump 71. The annular groove 31 is rotatable relative to the first slider bump 71, i.e., the movable barrel 30 is rotatable relative to the first slider bump 71. Specifically, the first slider bump 71 is embedded into the annular groove 31 of the movable barrel 30, and there is a gap between the first slider bump 71 and the wall of the annular groove 31.

Continuing with reference to FIGS. 2A to 2C, the first slider 70 is disposed within the fixing barrel 20, the first slider bump 71 extends to protrude out of the first line-type groove 24 to be coupled with the movable barrel 30. At the same time, the first slider bump 71 and the first line-type groove 24 can also serve as a guide for the first slider 70, and guide the first slider 70 to move proximally in the longitudinal direction of the fixing barrel 20. When the movable barrel 30 rotates, the annular groove 31 can rotate relative to the first slider bump 71, and meanwhile the annular groove 31 can prevent the relative movement between the first slider bump 71 and the movable barrel 30 along the longitudinal direction of the fixing barrel 20. Thus, when the movable barrel 30 makes a spiral motion, the movable barrel 30 drives the first slider bump 71 and the first slider 70 to move proximally in the longitudinal direction of the fixing barrel 20. After the first slider 70 is moved into contact engagement with (engaged with) the second slider 60, the rotation of the movable barrel 30 is continued, and the first slider 70 can drive the second slider 60 to move proximally along the longitudinal direction of the fixing barrel 20.

With reference to FIGS. 2A and 2B, the second slider 60 is provided with a second slider bump 61 that extends in a radial direction of the fixing barrel 20 to protrude out of the first line-type groove 24. The second slider bump 61 is slidable in the first line-type groove 24 to guide the second slider 60 to move proximally in the longitudinal direction of the fixing barrel 20.

The driving handle for recapturing an implant can convert the spiral motion of the movable barrel 30 into longitudinal linear motion of the first slider 70 and the second slider 60 through the cooperation of the inner protrusion 522 of the movable barrel 30 with the first outer spiral groove 521 of the fixing barrel 20, and the cooperation between the annular groove 31 of the movable barrel 30 and the first slider bump 71, thereby providing a driving force to the sheath tube 11 and recapturing tube 12. The handle allows the operator to apply a large longitudinal force to the second slider 60, to drive the second slider 60 and the recapturing tube 12 to move in the recapturing direction 200, in order to smoothly pull the recapturing tube 12, the recapturing net 121 (referring to FIG. 4A) and the captured implant into the catheter sheath 15 as shown in FIG. 1, reducing the difficulty of the recapturing operation.

With reference to FIG. 2B, before the first slider 70 moves into contact engagement with the second slider 60, the movable barrel 30 drives the first slider 70 to move, and the second slider 60 remains stationary, which is called a first stroke stage. After the first slider 70 moves into contact engagement with the second slider 60, the movable barrel 30 drives the first slider 70 to move together with the second slider 60, which is called a second stroke stage. In at least one, i.e. at least part, of the second stroke stage, the driving handle for recapturing an implant is required to convert the spiral motion of the movable barrel 30 into synchronous longitudinal motions of the first slider 70 and the second slider 60.

In some embodiments, the movement speed required by the movable barrel 30 in the first stroke stage is the same as that required in the second stroke stage. In some embodiments, the movement speed required by the movable barrel 30 during at least a portion of the first stroke stage is greater than the movement speed during the second stroke stage. In some embodiments, the movement speed required by the movable barrel 30 in the initial stage of the second stroke stage is similar to that of the first stroke stage.

In some embodiments, the length of the first outer spiral groove 521 is sufficiently long. In both the first and second stroke stages, the inner protrusion 522 engages the first outer spiral groove 521 in the entire strokes. In this case, in both stroke stages, the driving handle for recapturing an implant converts the spiral motion of the movable barrel 30 into longitudinal motion of the first slider 70, and also converts the spiral motion of the movable barrel 30 into synchronous longitudinal motion of the second slider 60 with the first slider 70 in the second stroke stage.

In other embodiments, the outer wall of the fixing barrel 20 may be provided with an inner protrusion mating structure. The inner protrusion mating structure and the first outer spiral groove 521 are distributed in sequence from distal to proximal in the recapturing direction 200.

Specifically, in some embodiments, the first outer spiral groove 521 is disposed corresponding to the second stroke stage, or the first outer spiral groove 521 is disposed corresponding to the second stroke stage and the end portion of the first stroke stage. The inner protrusion 522 on the movable barrel 30 moves in the longitudinal direction of the fixing barrel 20, and during at least one portion of the first stroke stage, the inner protrusion 522 may mate with the inner protrusion mating structure. In the second stroke stage, the inner protrusion 522 may mate with the first outer spiral groove 521. By providing such inner protrusion mating structure, the movement speed of the movable barrel 30 during at least a portion of the first stroke stage may be greater than the movement speed during the second stroke stage.

In other embodiments, the inner protrusion mating structure corresponds to the initial stage of the second stroke stage and the first stroke stage. By providing such inner protrusion mating structure, the movable barrel 30 may obtain a larger movement speed in both the first stroke stage and the initial stage of the second stroke stage.

In a preferred embodiment, the inner protrusion mating structure is disposed corresponding to the first stroke stage, and the first outer spiral groove 521 is disposed corresponding to the second stroke stage. In the first stroke stage, the movable barrel 30 provides a driving force to the first slider 70, the first slider 70 drives the sheath tube 11 to move proximally, the recapturing tube 12 remains stationary, and the distal end of the recapturing tube 12 and the recapturing net 121 are exposed from the distal end of the sheath tube 11, and the recapturing net 121 is released. In the second stoke stage, the first slider 70 moves together with the second slider 60, the movable barrel 30 provides a driving force for the movement of the first slider 70 and the second slider 60 through the cooperation of the inner protrusion 522 with the first outer spiral groove 521, so that the recapturing net 12 and the sheath tube 11 can both obtain a large longitudinal force, thus the recapturing net 121 and the captured implant are allowed to enter smoothly into the catheter sheath 15 as shown in FIG. 1.

With reference to FIGS. 2A and 2C, in some embodiments, the inner protrusion mating structure may include a sliding cylindrical surface 251. The sliding cylindrical surface 251 extends in the longitudinal direction of the fixing barrel 20. The inner protrusion 522 can slide on the sliding cylindrical surface 251 in the longitudinal direction of the fixing barrel 20. The sliding cylindrical surface 251 and the first outer spiral groove 521 are sequentially distributed along the recapturing direction 200. In the first stage, the movable barrel 30 is pulled in the longitudinal direction of the fixing barrel 20, and the movable barrel 30 provided with the inner protrusion 522 moves in synchronization with the first slider 70, such that the first slider 70 and the sheath tube 11 fixedly connected to the first slider 7 can obtain a large movement speed, so as to release the recapturing net 121 at a faster speed, thereby reducing the time of the surgical procedure. In this embodiment, speed regulation can be achieved, the sliding cylindrical surface 251 serves as a fast section, and the first outer spiral groove 521 serves as a slow section. In this way, not only the time of the surgical procedure can be reduced, but also the difficulty of pulling the recapturing net 121 and the captured implant into the catheter sheath 15 as shown in FIG. 1 can be reduced.

Figure 5A:
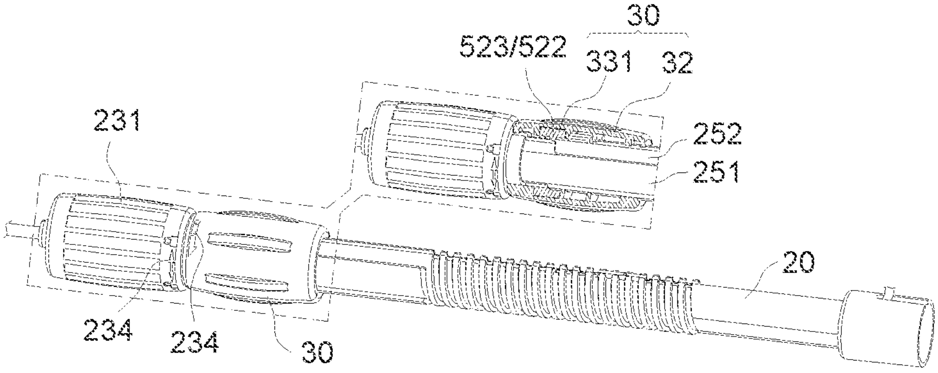
FIGS. 5A and 5B respectively show schematic diagrams of the handle of the first embodiment in the locked and unlocked states.
Figure 5B:
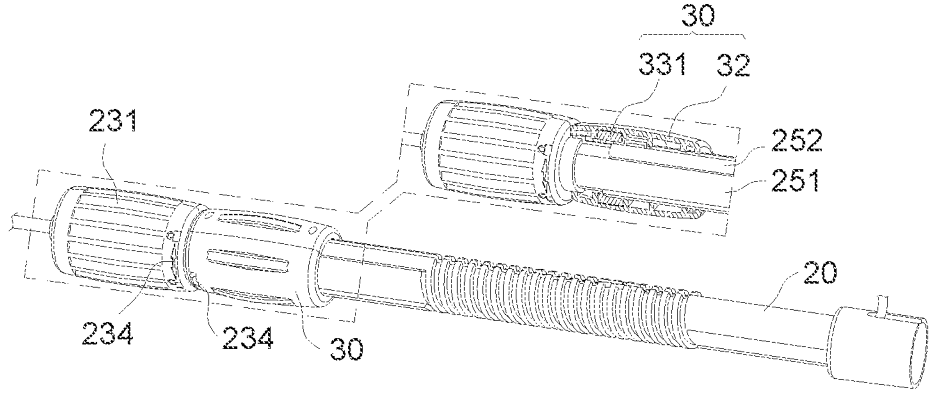

Further, the sliding cylindrical surface 251 may be provided with a longitudinal elongated rib 252 extending in the longitudinal direction of the fixing barrel 20. As shown in FIGS. 2C, 5A and 5B, the longitudinal elongated rib 252 can prevent the rotation of the inner protrusion 522 and guide the longitudinal movement of the inner protrusion 522 and the movable barrel.

As shown in FIG. 2C, in some embodiments, the inner protrusion 522 may be configured as an inner spiral rib 523. The inner spiral rib 523 matches with the first outer spiral groove 521. The inner spiral rib 523 can slide on the sliding cylindrical surface 251, and the inner spiral rib 523 has a large contact area with the first outer spiral groove 521, so that the movable barrel 30 can obtain a large driving force in the longitudinal direction of the fixing barrel 20 by rotating the movable barrel 30.

With reference to FIGS. 5A and 5B, the longitudinal elongated rib 252 provided on the sliding cylindrical surface 251 also serves to limit and lock the movable barrel 30. When the inner spiral rib 523 is located at the distal end side of the longitudinal elongated rib 252, the movable barrel 30 is rotated so that the inner spiral rib 523 comes into abutment with the distal end of the longitudinal elongated rib 252. As shown in FIG. 5A, the longitudinal elongated rib 252 can prevent the movable barrel 30 from moving in the longitudinal direction of the fixing barrel 20, and the movable barrel 30 is in a locked state. The movable barrel 30 is rotated so that the inner spiral rib 523 is offset from the longitudinal elongated rib 252. As shown in FIG. 5B, the movable barrel 30 is switched to the unlocked state, and the inner spiral rib 523 is movable on the sliding cylindrical surface 251 in the longitudinal direction of the fixing barrel 20. In this way, rotation of the movable barrel 30 can achieve locking and unlocking, and the operation is simple and reliable.

In some embodiments, the inner wall of the movable barrel 30 is provided with a plurality of inner spiral ribs 523, which are distributed at intervals in the circumferential direction. When the movable barrel 30 is rotated to a position where the longitudinal elongated rib 252 is positioned between two adjacent inner spiral ribs 523, the movable barrel 30 is in the unlocked state. Preferably, the number of the inner spiral ribs 523 is two. The central angle formed between the two inner spiral ribs 523 is 180°. There is an interval between the two inner spiral ribs 523. When the interval between the two inner spiral ribs 523 is rotated to be aligned with the longitudinal elongated rib 252, the movable barrel 30 is in the unlocked state.

In some embodiments, as shown in FIG. 2A, the movable barrel 30 and the fixing barrel 20 are cooperatively provided with a prompt sign 234 indicating an unlocked state and a locked state. Specifically, a prompt sign 234 is provided on the distal outer surface of the movable barrel 30. A grip 231 that is easy to grasp is provided at the distal end of the fixing barrel 20. The proximal outer surface of the grip 231 is provided with a prompt sign 234. With reference to FIGS. 5A and 5B, when the prompt sign 234 is at the position shown in FIG. 5A, the handle is in the locked state, and when the prompt sign 234 is at the position shown in FIG. 5B, the handle is in the unlocked state.

Figure 7A:
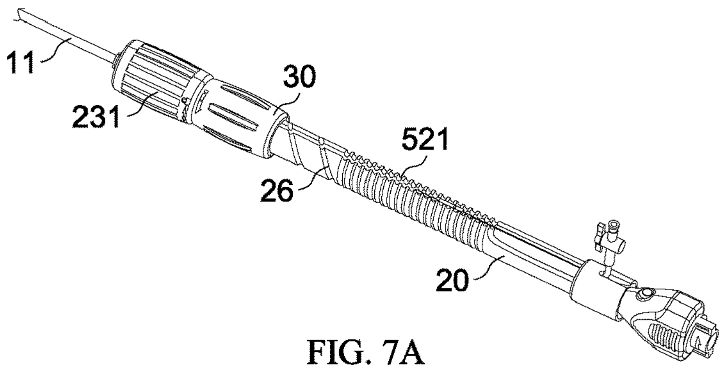
FIGS. 7A to 8B show schematic diagrams of the driving handle for recapturing an implant according to the first embodiment provided in this disclosure that is provided with another inner protrusion.

In the case where the inner protrusion mating structure includes the sliding cylindrical surface 251, the inner protrusion 522 may be configured as an inner spiral structure engaged with the first outer spiral groove 521, and the inner spiral structure may slide on the sliding columnar surface 251. In other embodiments, as shown in FIG. 7A, the inner protrusion mating structure may include a second outer spiral groove 26 disposed on the distal outer surface of the fixing barrel 20. The second outer spiral groove 26 and the first outer spiral groove 521 are sequentially distributed along the recapturing direction 200. The screw pitch of the second outer spiral groove 26 is greater than that of the first outer spiral groove 521. When the operator rotates the movable barrel 30, the movable barrel 30 moves faster on the second outer spiral groove 26, and the movable barrel 30 moves slower on the first outer spiral groove 521. In some embodiments, the second outer spiral groove 26 and the first outer spiral groove 521 are connected to form a variable pitch spiral groove, wherein the second outer spiral groove 26 serves as a fast section of the variable pitch spiral groove, and the first outer spiral groove 521 serves as a slow section thereof.

Specifically, with reference to FIGS. 7A to 8B, the inner protrusion 522 may be configured as a ball 524. The ball 524 may slide in the first outer spiral groove 521 or in the second outer spiral groove 26 and may move on the sliding cylindrical surface 251. The inner protrusion 522 is configured as a ball 524, which can reduce the resistance to the movement of the movable barrel 30 on the fixing barrel 20, and facilitate the smooth rotation or movement of the movable barrel 30. The inner protrusion 522 is configured as a ball 524, which is suitable for a case where the inner protrusion mating structure includes the sliding cylindrical surface 251, and also for a case where the inner protrusion mating structure includes the second outer spiral groove 26. As shown in FIGS. 7A to 8B, a second ring body 332 is disposed inside the movable barrel 30, a ball 524 is mounted on the second ring body 332, and the ball 524 can rotate in the second ring body 332.

In some embodiments, the outer surface of the fixing barrel 20 is provided with only one outer spiral groove in the longitudinal direction, and the second ring body 332 is provide with a ball 524 which moves within the outer spiral groove. In other embodiments, the outer surface of the fixing barrel 20 is provided with several outer spiral grooves in the longitudinal direction, and the several outer spiral grooves are uniformly distributed at intervals in the circumferential direction of the fixing barrel 20. Accordingly, the second ring body 332 is provided with the same number of balls 524 as the number of the outer spiral grooves, and each ball 524 corresponds to one outer spiral groove. The plurality of balls 524 are arranged to cooperate with a plurality of outer spiral grooves on the fixing barrel 20, which is favorable for increasing the contact area of the balls 524 with the fixing barrel 20, is convenient for the movable barrel 30 to obtain a large driving force in the longitudinal direction of the fixing barrel 20 by rotating the movable cylinder 30. However, as the number of the outer spiral grooves increases, the outer spiral grooves are too close to each other so that the fixing barrel 20 may not be able to withstand a large torque. Therefore, preferably, as shown in FIGS. 7A to 8B, the number of the balls 524 is three, and the three balls 524 are uniformly mounted on the second ring body 332 in the circumferential direction, that is, at an interval of 120°, and there are also three outer spiral grooves accordingly. Preferably, the outer spiral groove is provided as a variable pitch outer spiral groove. For example, the variable pitch outer spiral groove is composed of a second outer spiral groove 26 and a first outer spiral groove 521 which are sequentially distributed in the recapturing direction 200.

The structure of the inner protrusion 522 may have other embodiments. For example, the inner protrusion 522 may be a cylinder extending in the radial direction of the movable barrel 30. When the inner protrusion 522 moves into the first outer spiral groove 521, the cylindrical surface of the inner protrusion 522 is slidably engaged with the inner wall of the first outer spiral groove 521. When the inner protrusion 522 moves into the second outer spiral groove 26, it may also be slidably engaged with the inner wall of the second outer spiral groove 26.

Figure 6A:
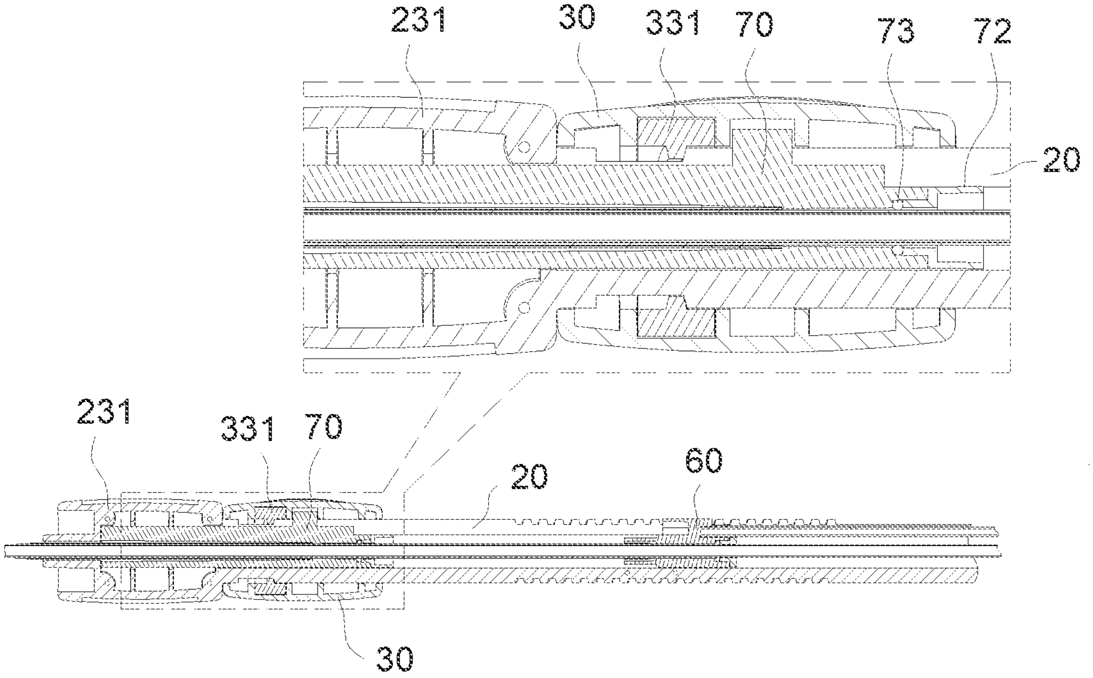
FIGS. 6A to 6D show schematic diagrams of the handle of the first embodiment in several operating states.
Figure 6B:
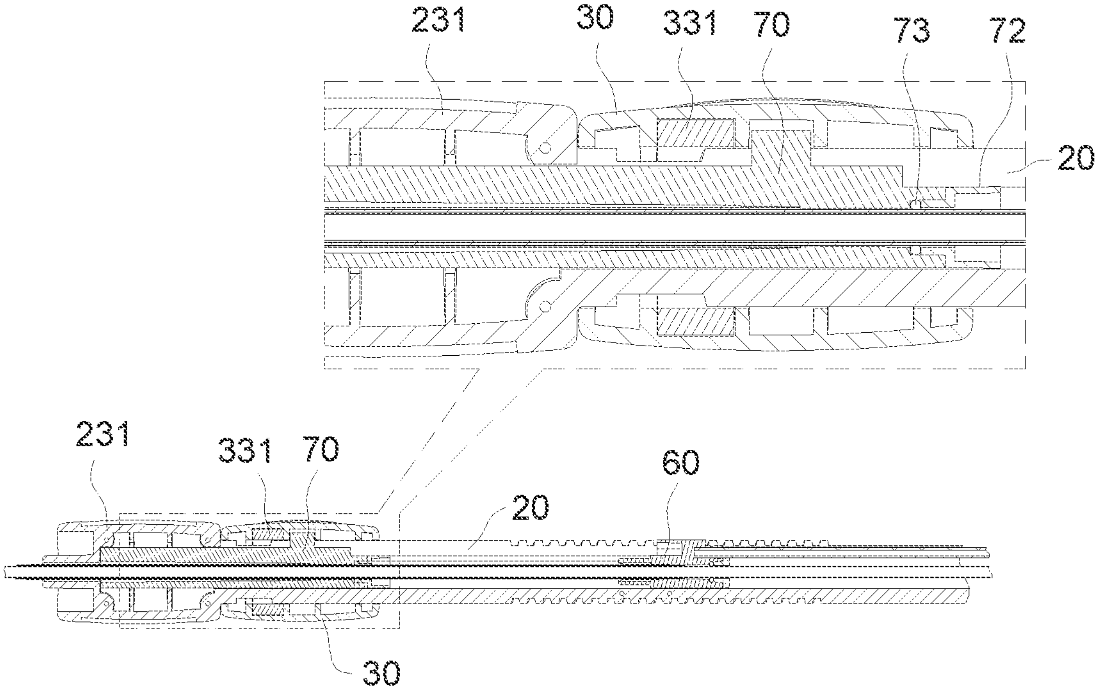
Figure 6C:
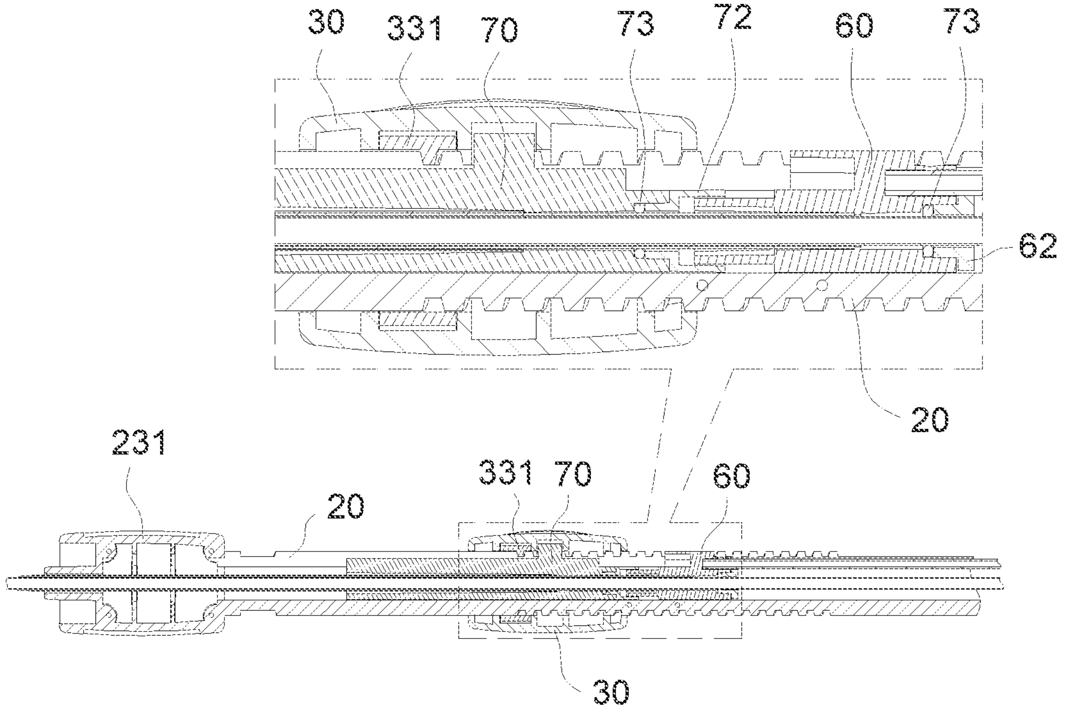
Figure 6D:
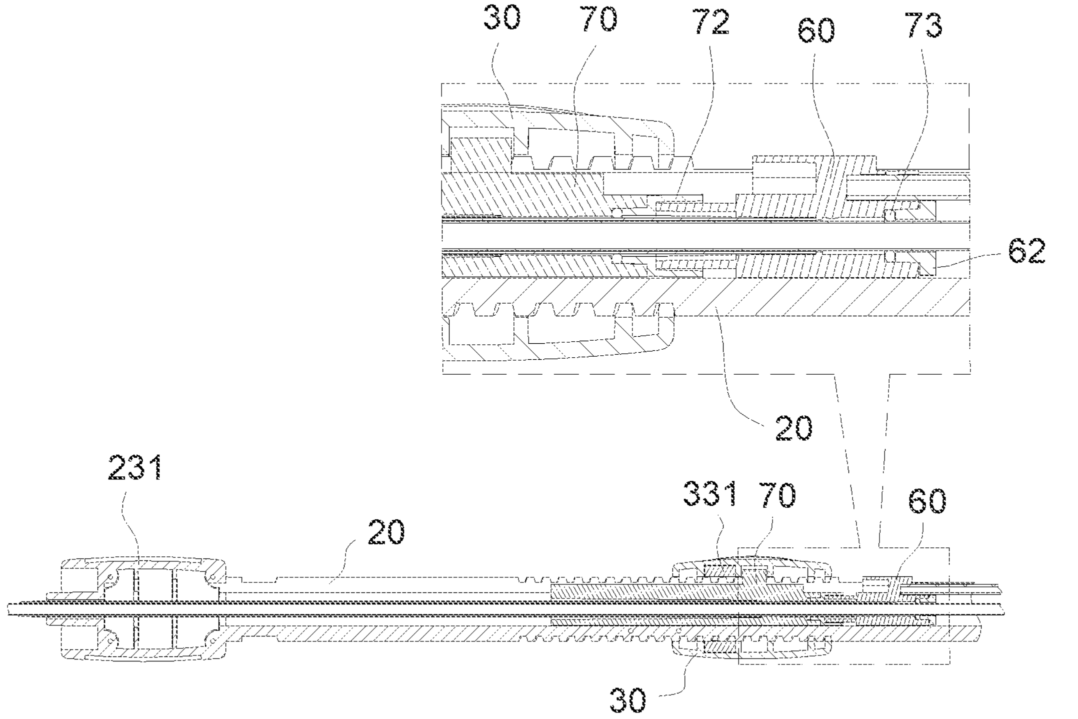

As shown in FIGS. 2B, 6C, and 6D, the first slider 70 is connected with a sheath tube piston cap 72 which is disposed at one end of the first slider 70 that is close to the second slider 60. The second slider 60 is provided with a flexible member 63, and a limiting groove 631 is provided on the side wall of the fixing barrel 20. The limiting groove 631 is configured to receive the flexible member 63 to limit the second slider 60 from moving in the recapturing direction with respect to the fixing barrel 20. The sheath tube piston cap 72 is configured to be able to disengage the flexible member 63 from the limiting groove 631 to release the limiting.

As shown in FIGS. 2B to 3C, the flexible member 63 can be snap fitted into the limiting groove 631 to prevent the net piston 60 from moving relative to the fixing barrel 20 in the recapturing direction 200. The sheath tube piston cap 72 is configured to be capable of sleeving outside the flexible member 63 such that the flexible member is retracted out of the limiting groove 631. Thus, in the process that the sheath tube piston 70 moves in the recapturing direction 200, before the sheath tube piston 70 contacts the net piston 60, the position of the net piston 60 is limited by the flexible member 63, which facilitates proximal movement of the sheath tube 11 relative to the recapturing tube 12, exposing and deploying the recapturing net 121 from the sheath tube 11. After the sheath tube piston cap 72 sleeves outside the flexible member 63, the sheath tube piston 70 is connected to the net piston 60 so as to be synchronously moved proximally.

Figure 3A:
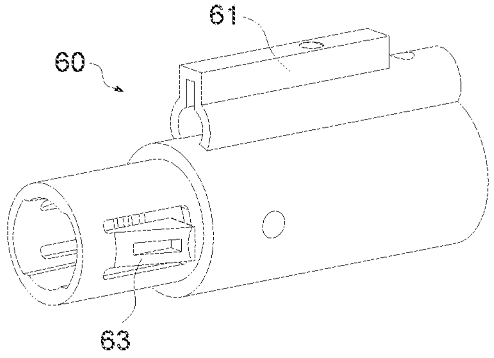
FIGS. 3A to 3C show schematic diagrams of a net piston for the handle of the first embodiment.
Figure 3B:
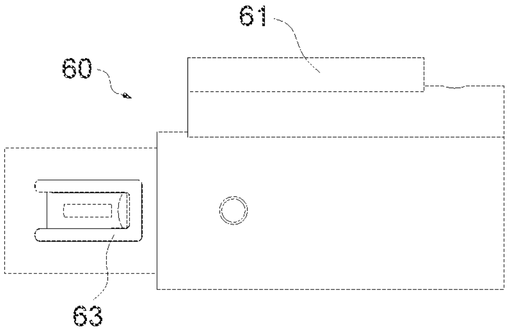
Figure 3C:
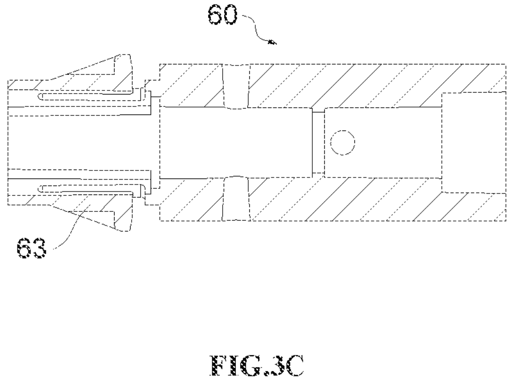

As shown in FIGS. 3A to 3B, the flexible member 63 may be of an integral structure with the net piston 60. The flexible member 63 is provided at the side wall of the net piston 60, and has a cantilevered end that protrudes outward. The flexible member 63 may have elasticity in its own material, and the cantilevered end can be contracted inward by the compression of the sheath tube piston cap 72.

In some embodiments, the inner wall of the fixing barrel 20 is provided with a limiting step 27. The limiting step 27 is configured to limit movement of the second slider 60 in the reverse direction to the recapturing direction 200 when being abutted by the second slider 60. As shown in FIG. 2C, when the second slider 60 abuts against the limiting step 27, the limiting step 27 prevents the second slider 60 from moving in the reverse direction to the recapturing direction 200.

Through the limiting step 27, the second slider 60 can be positioned, which is convenient for assembly. In the process of moving the second slider 60 in the reverse direction to the recapturing direction 200, at the same time when or after the flexible member 63 is snap fitted into the limiting groove 631, the second slider 60 abuts against the limiting step 27. The limiting step 27 and the flexible member 63 respectively limit the positions of the second slider 60 in two directions, so as to limit the position of the second slider 60.

In some embodiments, as shown in FIGS. 6A and 6B, a sealing ring 73 may be provided between the sheath tube piston cap 72 and the sheath tube piston 70. As shown in FIGS. 6C and 6D, a net piston cap 62 is connected to the proximal end of the net piston 60, and a sealing ring 73 may be provided between the net piston cap 62 and the net piston 60. By providing the sealing ring 73, it is possible to prevent the patient from bleeding excessively during the process of recapturing the implant. The sealing ring 73 serves as a hemostatic sealing assembly, and a soft silicone sealing ring 73 can be used.

In some embodiments, as shown in FIG. 2C, the movable barrel 30 includes a barrel body 32 and a first ring body 331 fixedly connected to an inner side of the barrel body 32, and the inner protrusion 522 is disposed on the first ring body 332. The outer surface of the first ring body 331 is provided with a connecting groove 341, and the inner surface of the barrel body 32 is provided by a connecting bump 342, so that the first ring body 331 is fixed integrally with the barrel body 32 through cooperation of the connecting groove 341 and the connecting bump 342. However, as to the fixed connection between the first ring body 331 and the barrel body 32, there may be other manners available for fixed connection, in addition to the cooperation of the connecting groove 341 and the connecting bump 342. It should be noted that the movable barrel 30 does not necessarily have to be provided with the independent first ring body 331, as long as it is provided with an inner protrusion 522.

In some embodiments, as shown in FIG. 2C, the barrel body 32 may take a two-lobed configuration, i.e., the barrel body 32 includes a first sub-barrel body 321 and a second sub-barrel body 322 which can be spliced into a complete barrel body 32.

In some embodiments, as shown in FIG. 2C, the fixing barrel 20 may take a two-lobed configuration, i.e., the fixing barrel 20 includes a third sub-barrel body 202 and a fourth sub-barrel body 203 which can be spliced into a complete barrel body structure. The first line-type groove 24 may be provided at the splicing of the third sub-barrel body 202 and the fourth sub-barrel body 203. As shown in FIGS. 2A to 2C and 7A, the distal end of the fixing barrel 20 is also provided with a grip 231, both the grip 231 and the movable barrel 30 are provided with easy-to-grip features. The medical staff can grasp the grip 231 to operate the movable barrel 30, such that the movable barrel 30 moves relative to the fixing barrel 20. The second slider 60 is provided with a flush tube 233, and the flush tube 233 is connected with a flush valve 2331. A fixing handle cap 232 is connected to the proximal end of the fixing barrel 20, and the fixing handle cap 232 has a groove that receives the flush tube 233.

Driving Handle for Recapturing an Implant in the Second Embodiment

Referring to FIGS. 9A to 13C, another driving handle for recapturing an implant is shown. In some embodiments, the handle includes a first slider 70, a second slider 60, a first fixing barrel 28, a first movable barrel 40 and a second movable barrel 30. The first slider 70 and the second slider 60 are sequentially distributed from distal to proximal in the longitudinal direction. The first fixing barrel 28 defines a tube passage 201 that is configured to receive the first slider 70 and the second slider 60. The first movable barrel 40 and the second movable barrel 30 sleeve outside the first fixing barrel 28 at an interval. The first movable barrel 40 is configured to rotatably move relatively to the first fixing barrel 28 in a first stroke stage to drive the first slider 70 to move linearly, and the second movable barrel 30 is configured to rotatably move relatively to the first fixing barrel 28 during at least a portion of a second stroke stage to drive the second slider 60 and the first slider 70 to move synchronously and linearly.

In some embodiments, such as the handle shown in FIGS. 9A to 13D, in the first stroke stage, the first slider 70 moves linearly and the second slider 60 remains stationary; in the second stroke stage, the second slider 60 and the first slider 70 move linearly in synchronization.

In other embodiments, the first movable barrel 40 is set to correspond to the initial stage of the second stroke stage and the first stroke stage. Accordingly, the first movable barrel 40 is configured to rotatably move with respect to the first fixing barrel 28 in the first stroke stage to drive the first slider 70 to produce a linear motion, and to rotatably move with respect to the first fixing barrel 28 during the initial stage of the second stroke stage to drive the second slider 60 and the first slider 70 to move synchronously and linearly. Accordingly, the second movable barrel 30 is configured to rotatably move with respect to the first fixing barrel 28 in the remaining stages other than the initial stage of the second stroke stage to drive the second slider 60 and the first slider 70 to move synchronously and linearly.

The driving handle for recapturing an implant is applied to the surgery of recapturing the implant via a catheter. The first slider 70 acts as a sheath tube piston and the second slider 60 acts as the net piston. The recapturing tube 12 and the sheath tube 11 can insert from the proximal end of the first fixing barrel 28, and pass out from the distal end of the first fixing barrel 28 and enter the blood vessel. The recapturing direction 200 is a direction in which the distal end of the first fixing barrel 28 is directed to the proximal end thereof. The proximal and distal ends are defined in a conventional manner of an implantation surgery, with the operator as the reference object, i.e. with the end close to the operator being the proximal end and the end remote from the operator being the distal end. The sheath tube piston 70 and the net piston 60 are sequentially distributed from distal to proximal in the recapturing direction 200.

In the driving handle for recapturing an implant shown in FIGS. 9A to 13C, the first fixing barrel 28 is provided with a second line-type groove 281 in the longitudinal direction. The first slider 70 is provided with a first outer protrusion 42, the second slider 60 is provided with a second outer protrusion 512, the first outer protrusion 42 and the second outer protrusion 512 extend in the radial direction of the first fixing barrel 28 to protrude out of the second line-typed groove 281.

Figure 9A:
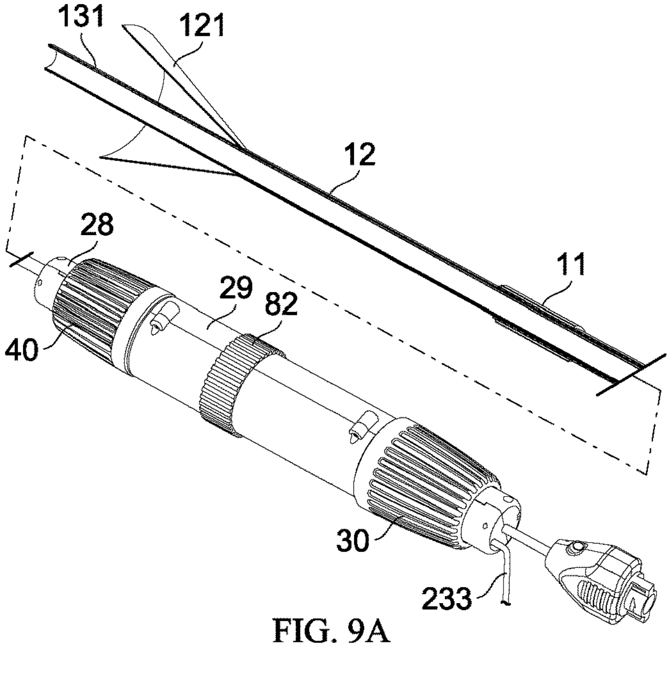
FIGS. 9A to 9C show schematic diagrams of a driving handle for recapturing an implant according to the second embodiment provided in this disclosure.
Figure 9B:
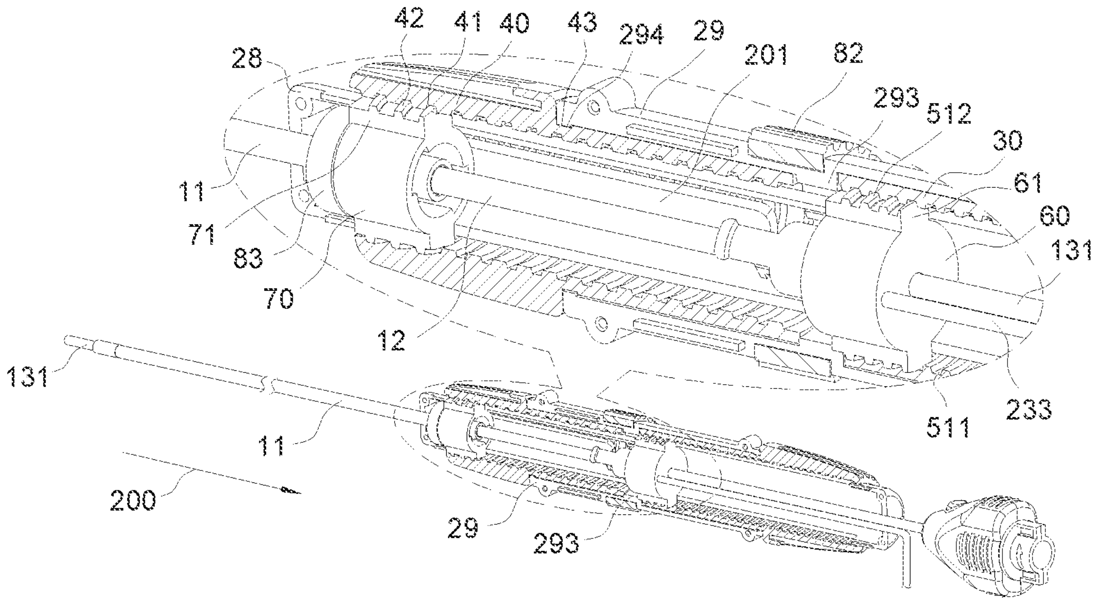
Figure 9C:
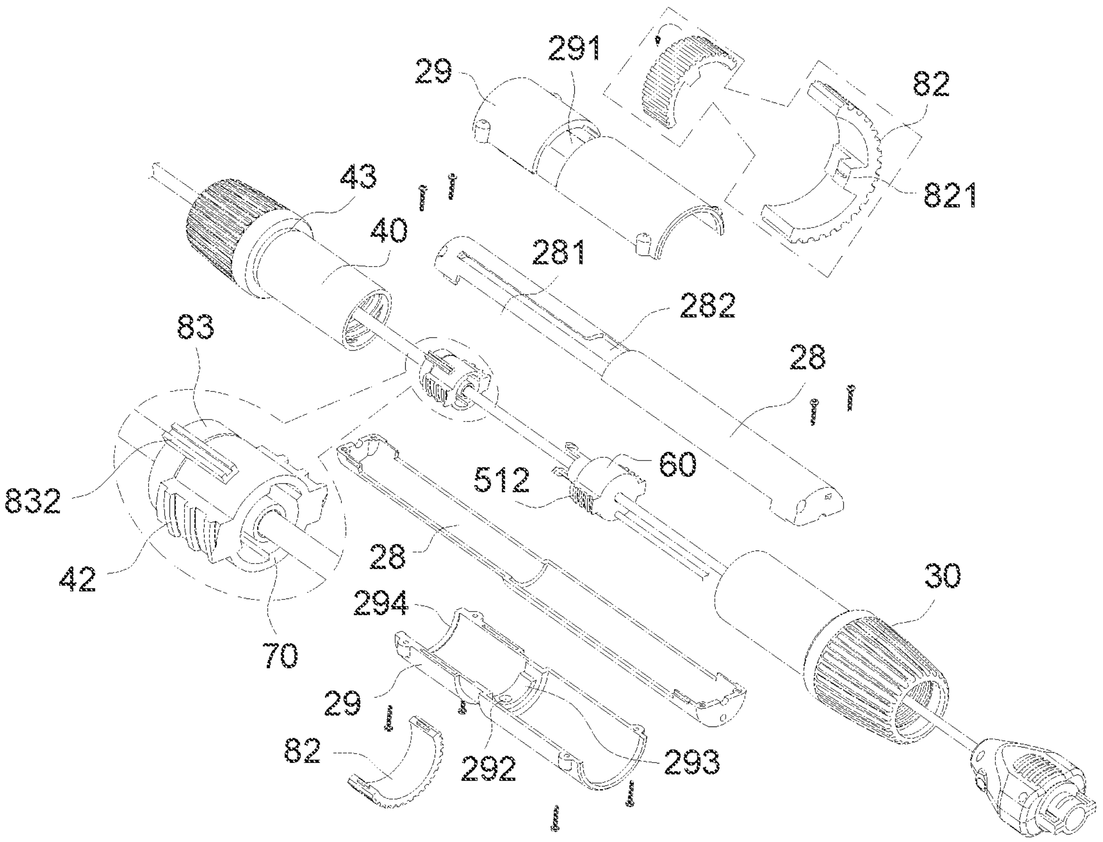

Referring to FIGS. 9A to 9C, the first movable barrel 40 and the second movable barrel 30 are rotatably mounted to the first fixing barrel 28, and the first movable barrel 40 and the second movable barrel 30 are restricted from moving in the longitudinal direction of the first fixing barrel 28. The inner wall of the first movable barrel 40 is provided with a first inner spiral groove 41, and the first outer protrusion 42 is adapted to move within the first inner spiral groove 41. The longitudinal movement of the first movable barrel 40 is restricted. When the first movable barrel 40 is rotated, the first outer protrusion 42 moves within the first inner spiral groove 41, to drive the first slider 70 to move longitudinally along the second line-type groove 281 on the first fixing barrel 28. The inner wall of the second movable barrel 30 is provided with a second inner spiral groove 511, and the second outer protrusion 512 is adapted to move within the second inner spiral groove 511. The longitudinal movement of the second movable barrel 30 is restricted. When the second movable barrel 30 is rotated, the second outer protrusion 512 moves within the second inner spiral groove 511, to drive the second slider 60 to move longitudinally along the second line-type groove 281 on the first fixing barrel 28.

The driving handle for recapturing an implant can: convert rotational movement of the first movable barrel 40 into longitudinal movement of a first slider 70 through cooperation between the first inner spiral groove 41 of the first movable barrel 40, the first outer protrusion 42 of the first slider 70, and the second line-type groove 281; and can convert rotational movement of the second movable barrel 30 into longitudinal movement of the second slider 60 and the first slider 70 through cooperation between the second inner spiral groove 511 of the second movable barrel 30, the second outer protrusion 512 of the second slider 60, and the second line-type groove 281. By the foregoing cooperation, as shown in FIG. 9B, the driving handle for recapturing an implant can provide a driving force to the sheath tube 11 and the recapturing tube 12. In contrast to directly pushing or pulling the recapturing tube 12 to make linear motion, the handle utilizes a spiral structure and allows the operator to apply a large longitudinal force to the second slider 60, to drive the second slider 60 and the recapturing tube 12 to move in the recapturing direction 200, in order to smoothly pull the recapturing tube 12, the recapturing net 121 and the captured implant into the catheter sheath 15 as shown in FIG. 1, reducing the difficulty of the recapturing operation.

Figure 10A:
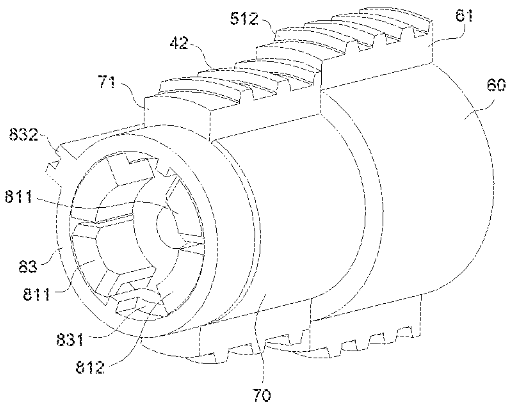
FIGS. 10A to 10C show schematic diagrams illustrating a relationship of a linkage cooperation between a net piston and a sheath tube piston in the handle according to the second embodiment.

In some embodiments, as shown in FIGS. 9B and 10A, the first outer protrusion 42 is configured as a first outer spiral rib 42 that mates with the first inner spiral groove 41. The first outer spiral rib 42 has a spiral shape mating with the first inner spiral groove 41, so that the first outer protrusion 42 has a large contact area with the second inner spiral groove 41, thereby it is favorable to convert the rotation of the first movable barrel 40 into a longitudinal movement of the first slider 70.

In some embodiments, as shown in FIGS. 9B and 10A, the second outer protrusion 512 is configured as a second outer spiral rib 512 that mates with the second inner spiral groove 511. The second outer spiral rib 512 has a spiral shape mating with the second inner spiral groove 511, so that the second outer protrusion 512 has a large contact area with the second inner spiral groove 511, thereby it is favorable to convert the rotation of the second movable barrel 30 into a longitudinal movement of the second slider 60 and the first slider 70.

In some embodiments, the screw pitch of the first inner spiral groove 41 is greater than that of the second inner spiral groove 511. The first inner spiral groove 41 corresponds to the first stroke stage as a fast section, and the second inner spiral groove 511 corresponds to the second stroke stage in as a slow section. Rotation of the first movable barrel 40 causes the sheath tube 11 to move in the recapturing direction 200 at a rapid speed during the first stroke stage so that the distal end of the recapturing net 121 and the recapturing net 121 are exposed from sheath tube 11 at the rapid speed. Rotation of the second movable barrel 30 causes the recapturing net 121 to move at a slow speed in the recapturing direction 200 during the second stroke stage, in order to provide a great pulling force to the recapturing tube 12 and the recapturing net 121, thus it is favorable to smoothly pull the recapturing net 121 into the catheter sheath 15 as shown in FIG. 1 together with the implant captured by the recapturing net 121.

In the case where the screw pitch of the first inner spiral groove 41 is greater than that of the second inner spiral groove 511, in other embodiments, the first inner spiral groove 41 on the first movable barrel 40 is sufficiently long. The first inner spiral groove 41 is arranged to correspond to the first stroke stage and the initial stage of the second stroke stage, and the second inner spiral groove 511 is arranged to correspond to the remaining stage except for the initial stage of the second stroke stage, and a faster movement speed than that in the remaining stage of the second stroke phase can be achieved in the first stroke phase and the initial stage of the second stroke phase.

Preferably, the number of the first outer protrusion 42 is of plural, and the plurality of first outer protrusions 42 are distributed at intervals along the longitudinal direction of the second fixing barrel 28 to increase the contact area of the first slider 70 with the first inner spiral groove 41, and this is convenient to apply a large driving force to the first slider 70. Similarly, the number of the second outer protrusions 512 is of plural to facilitate the application of a large driving force to the second slider 60.

The structure of the first outer protrusion 42 is not limited to the outer spiral rib 42. For example, the first outer protrusion 42 may also be a cylinder extending in the radial direction of the first movable barrel 40, and the cylinder extends into the first inner spiral groove 41. The cylindrical surface of the first outer protrusion 42 is slidably engaged with the inner wall of a first inner spiral groove 41. The structure of the second outer protrusion 512 is similar to this, and will not be described again.

As shown in FIGS. 9A to 9C and 10A, the first movable barrel 40 and the second movable barrel 30 sleeve outside the first fixing barrel 28; the first fixing barrel 28 is provided with a second line-type groove 281 extending in the longitudinal direction. The second slider 60 is disposed within the first fixing barrel 28. The second slider 60 is provided with a second slider bump 61. The second slider bump 61 is slidably provided in the second line-type groove 281. The second outer protrusion 512 is disposed on the top of the second slider bump 61. As shown in FIGS. 9B and 9C, the second slider bump 61 protrudes out of the second line-type groove 281, so that the second outer protrusion 512 at the top of the second slider bump 61 can be engaged with the second inner spiral groove 511 provided on the inner wall of the second movable barrel 30; and the second slider bump 61 is movable in the longitudinal direction of the first fixing barrel 28 within the second line-type groove 281, and guides the movement of the second slider 60 within the first fixing barrel 28.

The first slider 70 is disposed within the first fixing barrel 28, the first slider 70 is provided with a first slider bump 71, the first slider bump 71 is slidably provided in the second line-type groove 281, the first outer protrusion 42 is disposed on the top of the first slider bump 71, and the first slider bump 71 protrudes out of the second line-type groove 281 so that the first outer protrusion 42 can contact and engage with the first inner spiral groove 41; and the first slider bump 71 moves in the longitudinal direction within the second line-type groove 281, and guides the movement of the first slider 70 within the first fixing barrel 28.

In some embodiments, as shown in FIGS. 9B and 9C, the handle may include a first fixing barrel 28 and a second fixing barrel 29. The second fixing barrel 29 and the first fixing barrel 28 are both of a two-lobed configuration, and second fixing barrel 29 is fixedly connected to and sleeves outside the first fixing barrel 28. Specifically, a fixing hole 292 is provided inside a middle portion of the second fixing barrel 29 (see FIG. 9C), the outer surface of the middle portion of the first fixing barrel 28 is provided with a fixing post 283 (see FIG. 11), and the second fixing barrel 29 and the first fixing barrel 28 are fixedly connected through the engagement of the fixing hole 292 and the fixing post 283. A spacer 293 is provided in the middle portion of the inner peripheral wall of the second fixing barrel 29, and the fixing hole 292 is provided on the spacer 293. The spacer 293 of the second fixing barrel 29 allows the first movable barrel 40 and the second movable barrel 30 to sleeve outside the first fixing barrel 28 at interval, so as to longitudinally limit the first movable barrel 40 and the second movable barrel 30. Specifically, the spacer 293 is a spacer ring, as shown in FIG. 9C, which is an arc-shaped bump provided on the inner peripheral wall of the second fixing barrel 29.

Specifically, with continued reference to FIG. 9B, the proximal end of the first movable barrel 40 extends into the inner cavity at the left side of the spacer 293 of the second fixing barrel 29, the distal end of the second movable barrel 30 extends into the inner cavity at the right side of the spacer 293 of the second fixing barrel 29, and the distal end of the first movable barrel 40 and the proximal end of the second movable barrel 30 are both provided with easy-to-grip features. The outer surface of the middle portion of the first movable barrel 40 is provided with an annular positioning groove 43, the inner surface of the distal end of the second fixing barrel 29 is provided with positioning teeth 294, and the first movable barrel 40 and the second fixing barrel 29 can be longitudinally limited by the cooperation of the positioning groove 43 with the positioning teeth 294. For example, there is a gap between the positioning teeth 294 and the positioning groove 43 in the radial direction, and when the first movable barrel 40 is rotated, the positioning groove 43 can rotate relative to the positioning tooth 294. Similarly, the second movable barrel 30 and the second fixing barrel 29 can be longitudinally limited through teeth-groove cooperation. The second fixing barrel 29 and the first fixing barrel 28 fix the first movable barrel 40 and the second movable barrel 30 to be rotatable and at an interval between the second fixing barrel 29 and the first fixing barrel 28, thereby facilitating assembly, and the stability of the structure can be improved.

Figure 10B:
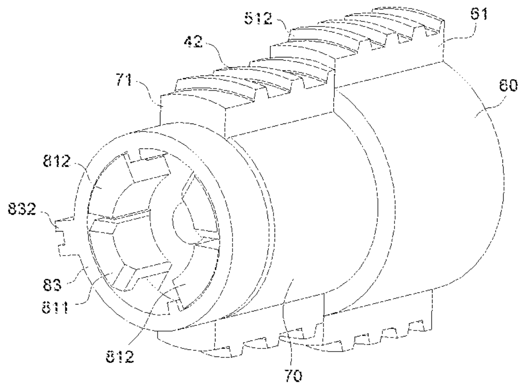
Figure 10C:
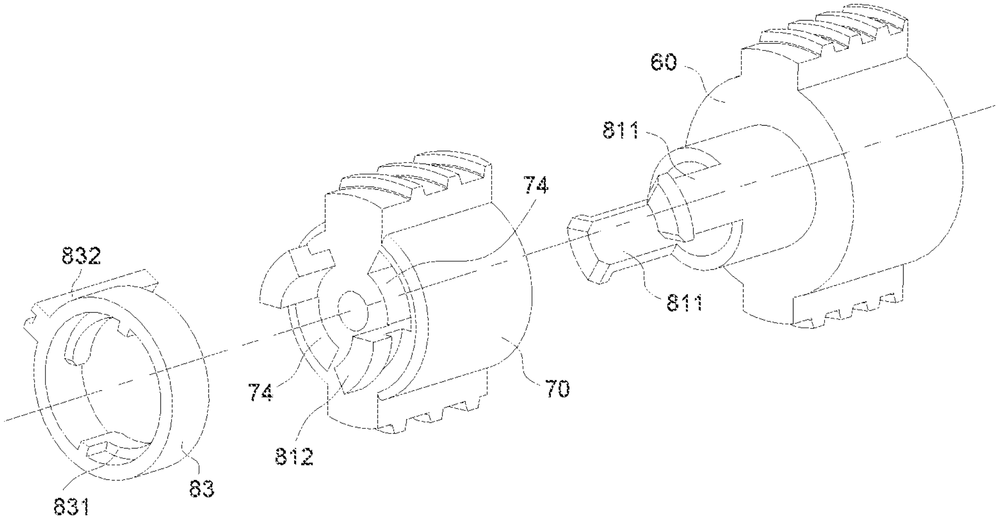
Figure 11:
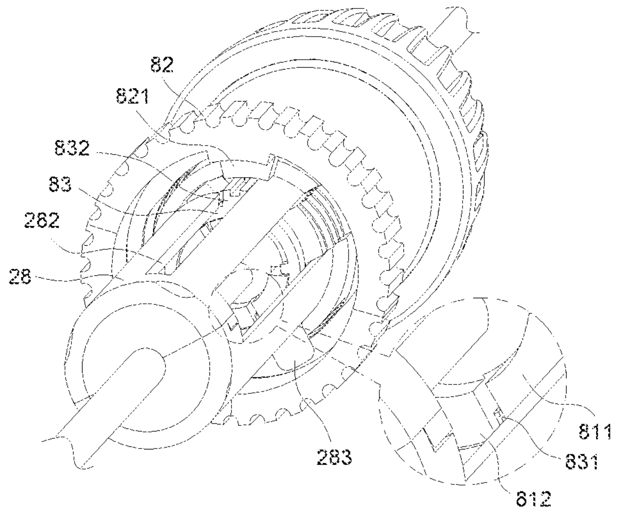
FIG. 11 is a schematic diagram showing the connection of a first fixing barrel, a knob and a locking ring in the handle of the second embodiment.

When recapturing the implant by using the driving handle for recapturing an implant, the first slider 70 first drives the sheath tube 11 to move in the recapturing direction 200 to release the recapturing net 121. After the recapturing net 121 captures the implant, both the recapturing tube 12 and the sheath tube 11 can move in the recapturing direction 200 to be pulled into the catheter sheath 15 as shown in FIG. 1. Preferably, after the recapturing net 121 captures the implant, the recapturing tube 12 moves in the recapturing direction 200 in synchronization with the sheath tube 11. In some embodiments, as shown in FIGS. 10A to 10C, the first slider 70 is provided with a longitudinal through hole 74. The first slider 70 is further provided with a rotatable locking ring 83, and a locking ring inner bump 831 is provided on the inner side of the locking ring. The second slider 60 is provided with a second claw 811 which is able to pass through the longitudinal through hole 74, for example, the second claw 811 passes through the longitudinal through hole 74 during the engagement of the first slider 70 with the second slider 60. As shown in FIG. 11, a rotatable knob 82 is disposed on the outer periphery of the first fixing barrel 28, and when the knob 82 rotates, the locking ring 83 can be driven to rotate until the second claw 811 engages with the locking ring inner protrusion 831. When the handle is provided with the second fixing barrel 29, as shown in FIGS. 9B and 9C, the knob 82 sleeves outside the second fixing barrel 29.

As shown in FIG. 11, when the knob 82 is rotated, the knob 82 drives the locking ring 83 to rotate together, such that the second claw 811 are brought into abutment with the distal end of the locking ring inner bump 831, and the second claw 811 is engaged with the locking ring inner bump 831. Since the locking ring 83 is longitudinally fixed on the first slider 70, in this case, as shown in FIGS. 12C to 12D and 13C to 13D, during the proximal movement of the second slider 60 and the second claw 811, the first slider 70 is able to move in the recapturing direction 200 synchronously with the second slider 60.

Figure 12D:
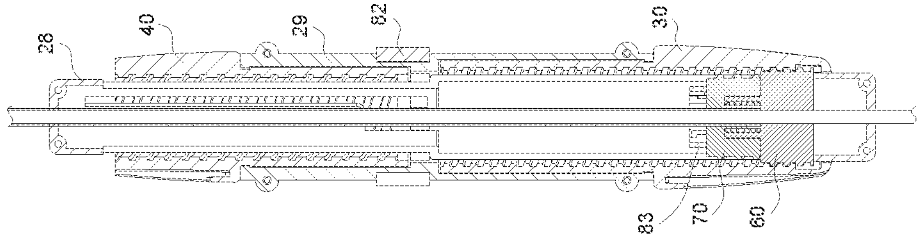
FIGS. 12A to 12D and FIGS. 13A to 13D show schematic diagrams of the handle of the second embodiment in several operating states.
Figure 12C:
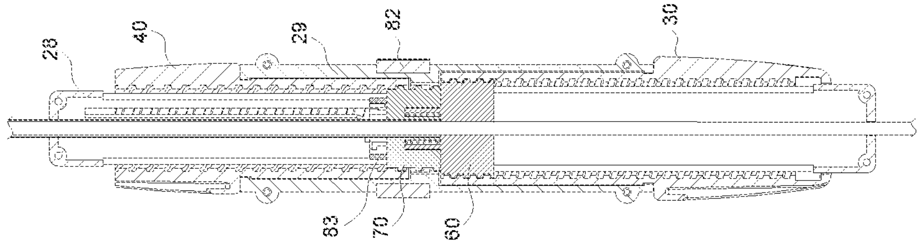
Figure 12B:
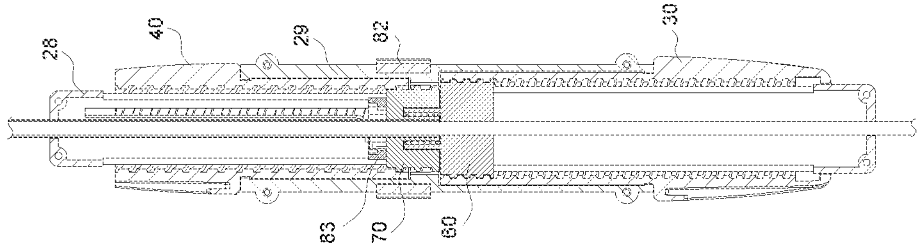
Figure 12A:
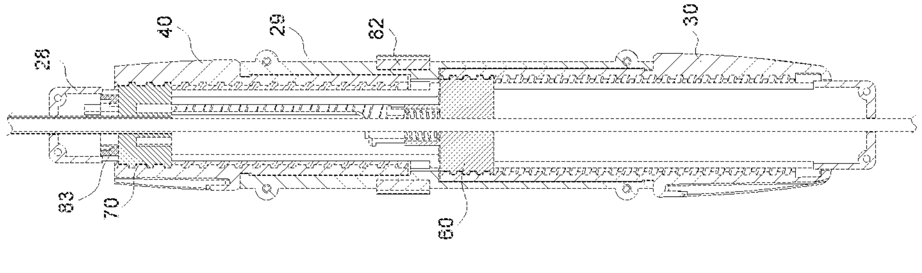
Figure 13D:
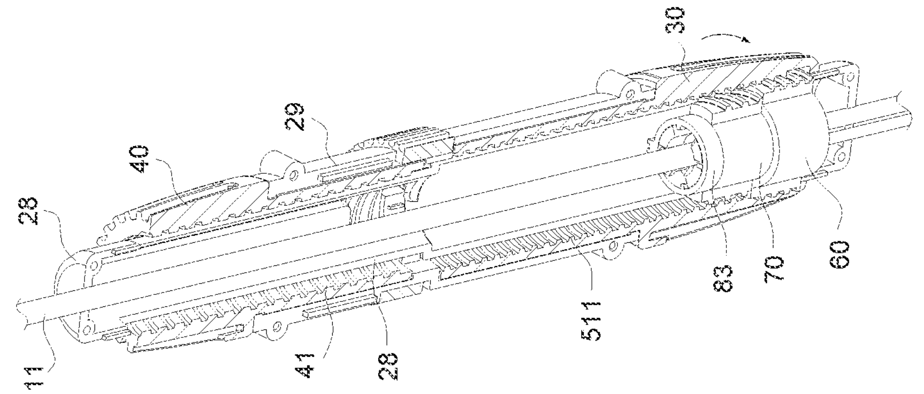
Figure 13C:
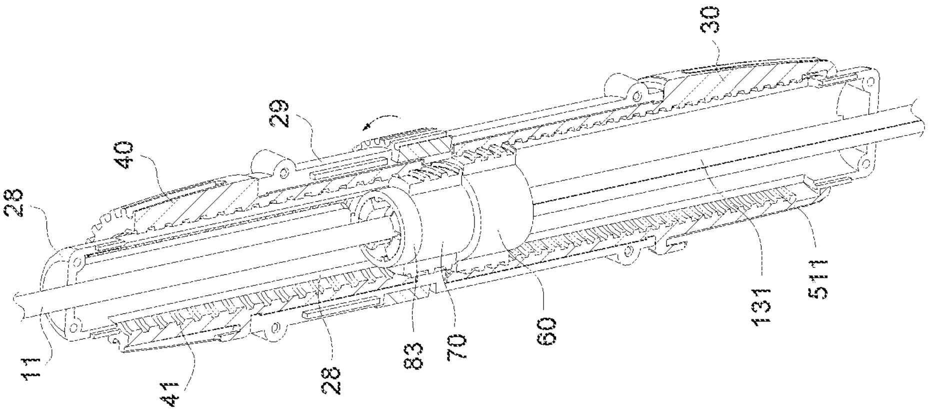
Figure 13B:
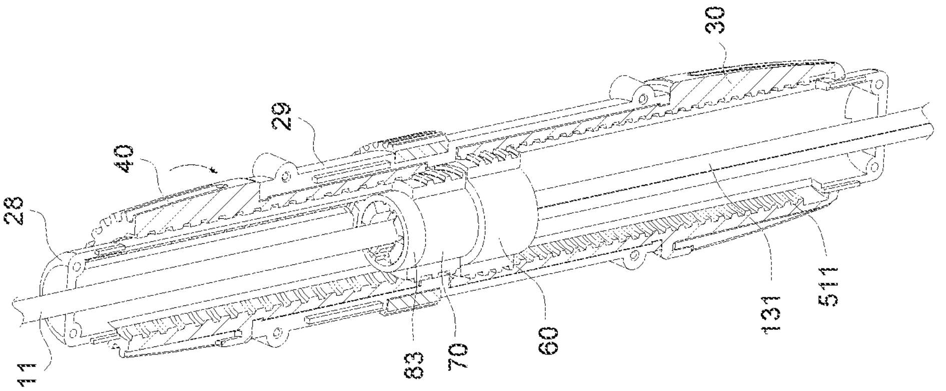
Figure 13A:
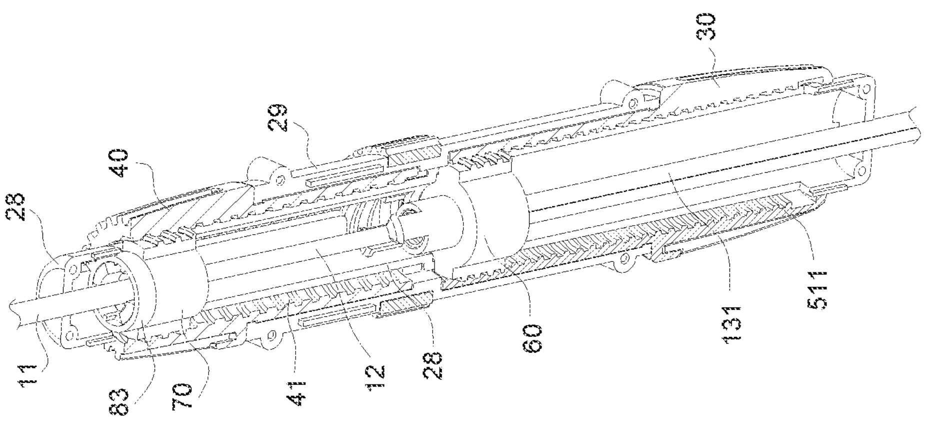

As shown in FIGS. 12A and 13A, before the first slider 70 and the second slider 60 are engaged together, the first slider 70 and the second slider 60 may move independently, i.e., relative movement may occur therebetween. For example, the first movable barrel 40 is operated to bring the first slider 70 to be closer to the second slider 60, and the second claw 811 will penetrate into the longitudinal through hole 74. As shown in FIGS. 12B and 13B, after the first slider 70 moves toward the second slider 60 beyond the stroke of the first inner spiral groove 41, the first slider 70 is no longer restrained by the first inner spiral groove 41; meanwhile, the second claw 811 penetrates into the longitudinal through hole 74 and moves to the distal end side of the locking ring inner bump 831. As shown in FIGS. 12C and 13C, when the knob 82 is rotated, the knob 82 drives the locking ring 83 to rotate such that the second claw 811 is engaged with, fastened to, or abutted on the locking ring inner bump 831. The first slider 70 and the second slider 60 are engaged together by the locking ring inner bump 831, and thus, the first slider 70 can move together with the second slider 60.

Specifically, as shown in FIGS. 10A to 10C, a protrusion is provided on the outer side of the distal end of the second claw 811. When the second claw 811 is engaged with the locking ring inner bump 831, the main body portion of the second claw 811 is located at an inner side of the locking ring inner bump 831. The protrusion is located between the locking ring inner bump 831 and the distal end of the locking ring 31, so that the second claw 811 is fastened to the locking ring inner bump 831.

The locking ring 83 is rotatably provided on the first slider 70. The locking ring 83 is capable of moving together with the first slider 70, and it is able to rotate relative to the first slider 70. The locking ring 83 may be provided at a distal end side of the first slider 70. As shown in FIGS. 10A to 10C, the first slider 70 is provided with a first claw 812. At the time of assembly, the first claw 812 can be engaged with the locking ring inner bump 831 by rotating the locking ring 83 or the first slider 70. As shown in FIGS. 10A and 10B, the first claw 812 and the second claw 811 are offset in the circumferential direction. Before the second claw 811 is engaged with the locking ring inner bump 831, as shown in FIG. 10A, only the first claw 812 is fastened to the locking ring inner bump 831 and the locking ring 83 can move together with the first slider 70. By configuring the locking ring inner bump 831 to have an appropriate length in the circumferential direction, when the locking ring 83 and the locking ring inner bump 831 are rotated, both the first claw 812 and the second claw 811 can be fastened to the locking ring inner bump 831. As shown in FIG. 10B, the first slider 70 is thereby brought into engagement with the second slider 60. Further, the locking ring inner bump 831 has an L-shape, which can prevent the locking ring 83 from being excessively rotated, and prevent the first claw 812 from being disengaged from the locking ring inner bump 831 due to excessive rotation of the locking ring 83.

Referring to FIG. 9C, when the handle is provided with the second fixing barrel 29, in some embodiments, the side wall of the second fixing barrel 29 is provided with a knob through hole 291, the knob 82 is provided with a knob bump 821 passing through the knob through hole 291. The first fixing barrel 28 is provided with a longitudinally extending third line-type groove 282, the outer side of the locking ring 83 is provided with the locking ring outer bump 832. The locking ring outer bump 832 extends to protrude out of the third line-type groove 282 and can cooperate with the knob bump 821 in a manner of groove tenon to achieve engagement between the locking ring 83 and the knob 82. As shown in FIGS. 9C, 12B and 13B, in the case where the locking ring 83 moves longitudinally into alignment with the knob bump 821 of the knob 82, the knob bump 821 is connected with the locking ring outer bump 832, so as to realize that the knob 82 drives the locking ring 83 to rotate.

In some embodiments, as shown in FIG. 10A, the top surface of the locking ring outer bump 832 is provided with a longitudinally extending groove portion. The knob bump 821 is provided with a protrusion which cooperates with the groove portion. When the locking ring outer bump 832 moves in the third line-type groove 282 in the recapturing direction 200, as shown in FIG. 11, the protrusion of the knob bump 821 can slide into the groove portion of the locking ring outer bump 832, such that rotation of the knob 82 can drive the locking ring 83 to rotate together. In other embodiments, the locking ring 83 and the knob 82 may be engaged by providing a protrusion on the locking ring outer bump 832 and providing a groove portion on the knob bump 821.

The locking ring outer bump 832 extends beyond the side wall of the first fixing barrel 28 through the third line-type groove 282. The knob bump 821 extends through the knob through hole 291 to the inner cavity of the second fixing barrel 29, so as to facilitate the engagement of the knob bump 821 and the locking ring outer bump 832. The third line-type groove 282 also serves to guide the movement of the locking ring outer bump 832 and the locking ring 83. In some embodiments, as shown in FIG. 9C, the third line-type groove 282 is configured in an L-shape. On the one hand, during the movement of the locking ring 83 with the first slider 70 toward the second slider 60, the third line-type groove 282 limits deflection of the locking ring outer bump 832 and the locking ring 83, so that the protrusion on the knob bump 821 can slide into the groove portion of the locking ring outer bump 832, thereby improving the stability of the operation. On the other hand, when the locking ring 83 and the first slider 70 move to the position where they are engaged with the second slider 60, the L-shaped third line-type groove 282 may reserve a space for the locking ring outer bump 832 and locking ring 83 to rotate with the knob 82.

The manner of engagement of the locking ring 83 with the first slider 70 is not limited to the above-described embodiment in which the first claw 812 cooperates with the locking ring inner bump 831, as long as the relative position of the locking ring 83 with respect to the first slider 70 in the longitudinal direction is limited and they are relatively rotatable about the axis. For example, the locking ring 83 is configured to provide an arc-shaped groove on its end surface facing the first slider 70. The first slider 70 is provided with a feature extending into the arc-shaped groove. The arc-shaped groove and the feature cooperate such that the locking ring 83 is rotatably disposed on the first slider 70. Specifically, the arc shape of the arc-shaped groove is an arc shape centering on the intersection point of the locking ring axis and the end face of the locking ring, and the central angle of this arc shape may be 60°. The feature may be a convex portion slidably disposed in the arc-shaped groove, and the convex portion is limited in the arc-shaped groove to keep the longitudinal movement of the locking ring 83 consistent with the longitudinal movement of the first slider 70. More specifically, the cross section of the arc-shaped groove may be T-shaped, and the convex portion may be a T-shaped block. In the above-described embodiment, the arc-shaped groove is provided on the end face of the locking ring 83 facing the first slider 70, and besides, the arc-shaped groove may also be provided on the inner side of the locking ring 83. The feature on the first slider 70 is arranged in a similar manner to cooperate with the arc-shaped groove. In this embodiment, when the locking ring 83 and the locking ring inner bump 831 are rotated, only the second claw 811 is engaged with the locking ring inner bump 831.

In addition to achieving the engagement of the first slider 70 with the second slider 60 by means of the locking ring 83, other means may also be used. For example, the proximal end of the first slider 70 is provided with a buckle, and the distal end of a second slider 60 is provided with a buckling groove for engaging with the buckle. When the first slider 70 moves close to the second slider 60, the buckle and the buckling groove are buckled together, so that the first slider 70 and the second slider 70 can be engaged.

It should be noted here that the handle does not necessarily include the second fixing barrel 29. When the handle includes only the first fixing barrel 28, the first fixing barrel 28 doesn't need to be provided with the fixed post 283. At this time, the knob 82 rotatably sleeves outside the first fixing barrel 28 relative to the first fixing barrel 28. Specifically, the knob 82 and the first fixing barrel 28 may be fixed through teeth-groove cooperation. In some embodiments, the spacer may be an arc-shaped bump provided in the middle portion of the outer peripheral wall of the first fixing barrel 28, for separating the first movable barrel 40 from the second movable barrel 30 and for longitudinally limiting the same. In some embodiments, peripheries of both the proximal end and the distal end of the first fixing barrel 28 may be removably provided with limiting rings. The spacer cooperates with the two limiting rings to further limit the longitudinal movement of the first movable barrel 40 and the second movable barrel 30.

The driving handle for recapturing an implant provided by the present disclosure has been described above. During at least part of the stroke in which the recapturing tube 12, the recapturing net 121 and the captured implant are pulled into the catheter sheath 15 as shown in FIG. 1, the handle shown in FIGS. 2A to 8B and the handle shown in FIGS. 9A to 13D, the first slider 70 and the second slider 60 all make synchronous linear motion. During at least part of the stroke in which the recapturing tube 12, the recapturing net 121 and the captured implant are pulled into the catheter sheath 15 as shown in FIG. 1, the handle shown in FIGS. 2A to 8B is driven by a spiral motion of the movable barrel 30 (the spiral motion is a combination of a rotary motion and a linear motion), and the rotary motion is converted into a linear motion, so as to drive the first slider 70 and the second slider 60 to perform synchronous linear motion. The handle shown in FIGS. 9A to 13D is driven by a rotary motion of the second movable barrel 30, and the rotary motion is converted into a linear motion, so as to drive the first slider 70 and the second slider 60 to perform synchronous linear motion.

Accordingly, during at least part of the stroke in which the recapturing tube 12, the recapturing net 121 and the captured implant are pulled into the catheter sheath 15 as shown in FIG. 1, the handle shown in FIGS. 2A to 8B and the handle shown in FIGS. 9A to 13D both drive the first slider 70 and the second slider 60 by converting the rotary motion into the linear motion. In contrast to a driving handle for recapturing an implant which directly pushes the first slider 70 and the second slider 60 to make linear motion, the driving handle for recapturing an implant provided in the present disclosure is more convenient for medical staff to apply a greater longitudinal driving force to the first slider 70 and the second slider 60, which is favorable to smoothly pull the sheath tube 11, the recapturing net 121 and captured implant into the catheter sheath 15 as shown in FIG. 1.

The driving handle for recapturing an implant may be applied to recapturing of a heart valve prosthesis in a catheter-implanted heart valve prosthetic procedure. The driving handle for recapturing an implant may also be applied to other procedures for recapturing implants or other procedures involving similar operation.

Implant Recapturing Apparatus

With reference to FIGS. 2A to 2C, 7A to 7B and 9A to 9C, an implant recapturing apparatus is shown, and the implant recapturing apparatus may comprise a recapturing net 121, a recapturing tube 12, a sheath tube 11 and the driving handle for recapturing an implant as described above. The recapturing tube 12 and the sheath tube 11 are slidably provided in the tube passage 201. The sheath tube 11 sleeves outside the recapturing tube 12, and the distal end of the recapturing tube 12 is connected to the recapturing net 121. The proximal end of the sheath tube 11 is connected to the first slider 70 and the proximal end of the recapturing tube 12 is connected to the second slider 60.

In some embodiments, the recapturing apparatus further includes an inner tube 131 and a hemostatic valve device 132 disposed at the proximal end of the inner tube 131, and the inner tube 131 penetrates through the recapturing tube 12. In some cases, no catheter is provided outside the positioning guide wire to which the implant is connected, and the positioning guide wire penetrates through the inner tube 131 to extend out from the proximal end of the hemostatic valve device 132.

Figure 4A:
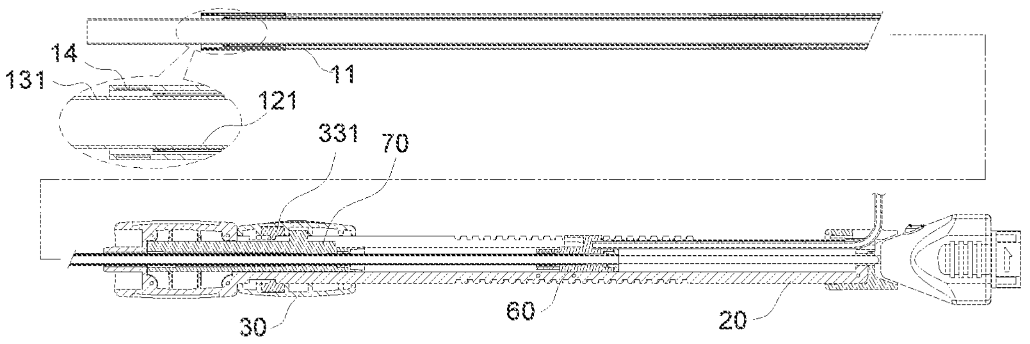
FIGS. 4A and 4B respectively show schematic diagrams of the handle of the first embodiment before and after the unfolding of the recapturing net.
Figure 4B:
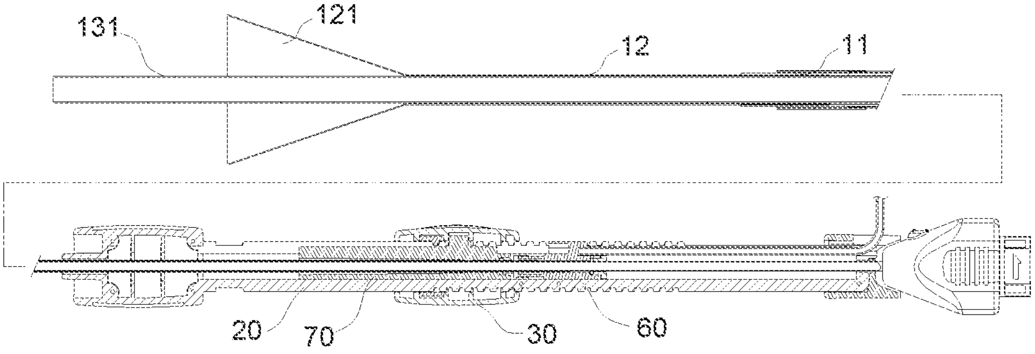

In some embodiments, as shown in FIG. 4A, the distal end of the sheath tube 11 is provided with a development marker 14, which is made of a radiopaque material. By providing the development marker 14, it is helpful to observe the relative sliding length between the sheath tube 11 and the recapturing tube 12 in real time during the implant recapturing process. In order to prevent the development marker 14 from falling off, the development marker 14 may be embedded in the wall of the sheath tube, or be tightly sleeved onto the sheath tube 11, or a shallow groove may be provided on the sheath tube 11 to accommodate the development marker 14. The development marker 14 may be a metal ring. The material of the development marker 14 may be platinum, gold, iridium, palladium, rhenium, rhodium, tungsten, tantalum, silver and tin. The development marker 14 may also be a polymer containing radiopaque particles. The radiopaque particles may be platinum, gold, iridium, palladium, rhenium, rhodium, tungsten, tantalum, silver and tin, or other contrast agents commonly used in the art. The polymer is selected from the group consisting of Pebax, poly(ether-urethane), polyester copolymer, olefin-derived copolymer, natural rubber, synthetic rubber, thermoplastic elastomer 63, specialty polymers, polyurethanes and nylons.

Implant Recapturing Method

The present disclosure provides an implant recapturing method using the above-described driving handle for recapturing an implant, wherein the catheter sheath 15 shown in FIG. 1 sleeves outside the sheath tube 11. The recapturing method comprises: a step S10 in which the sheath tube 11 is moved proximally, and the recapturing net 121 to which the distal end of the recapturing tube 12 is connected is exposed (released) from the sheath tube 11 and deployed; a step S20 in which the recapturing net 121 captures the implant to be recaptured; a step S30 in which the implant, the recapturing net 121 and the recapturing tube 12 are all moved proximally, and are all pulled back into the catheter sheath 15 as shown in FIG. 1.

Specifically, when the implant is recaptured using the handle shown in FIGS. 2A to 2C, in the step S10, referring to FIG. 6C, the movable barrel 30 is pulled proximally to drive the sheath tube 11 to move proximally; in the step S30, referring to FIG. 6D, the movable barrel 30 is rotated to drive the sheath tube 11, the recapturing net 121 and the recapturing tube 12 to move together proximally.

Figure 7B:
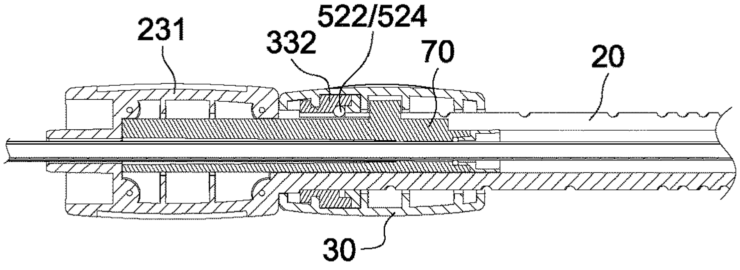
Figure 8A:
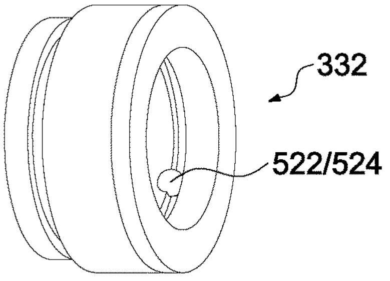
Figure 8B:
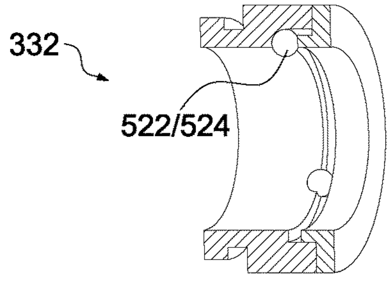

When the implant is recaptured using the handle shown in FIGS. 7A to 7B, in the step S10, the movable barrel 30 is rotated to drive the sheath tube 11 to move proximally; in the step S30, the rotation of the movable barrel 30 is continued to drive the sheath tube 11, the recapturing net 121 and the recapturing tube 12 to move together proximally.

When the implant is recaptured using the handle shown in FIGS. 9A to 9C, in the step S10, referring to FIGS. 12A to 12B and 13A to 13B, the first movable barrel 40 is rotated to drive the sheath tube 11 to move proximally; in the step S30, referring to FIGS. 12C and 13C, firstly the knob 82 is rotated to engage the first slider with the second slider, then referring to FIGS. 12D and 13D, the second movable barrel 30 is rotated to drive the sheath tube 11, the recapturing net 121, and the recapturing tube 12 to move proximally.

In the various steps S30 described above, as shown in FIGS. 6D, 12D and 13D, the sheath tube 11 moves proximally together with the recapturing tube 12 so as to pull the recapturing tube 12, the sheath tube 11 and the recapturing net 121 together into the catheter sheath 15 as shown in FIG. 1.

The longitudinal direction in the above embodiment specifically refers to the length direction of the handle. The foregoing are only several embodiments of the present disclosure, and those skilled in the art may make various modifications or variations to the embodiments of the present disclosure according to the disclosure of the application documents without departing from the spirit and scope of the present disclosure.

What is claimed is:

1. An implant recapturing method, comprising:

providing an implant recapturing apparatus which includes a driving handle for recapturing an implant, a recapturing net, a recapturing tube and a sheath tube, the handle including a first movable barrel and a second movable barrel;

rotating the first movable barrel to drive the sheath tube to move proximally, thereby releasing and unfolding the recapturing net at the distal end of the recapturing tube; and rotating the second movable barrel to drive the recapturing tube, the recapturing net, the implant, and the sheath tube together to move proximally into the catheter sheath.

2. The recapturing method according to claim 1, wherein the handle further comprises a knob, a first slider connected to the sheath tube, and a second slider connected to the recapturing tube, and wherein the method further comprises rotating the knob to engage the first slider with the second slider prior to rotating the second movable barrel so as to enable the recapturing tube to move together with the sheath tube.

3. The recapturing method according to claim 2, wherein:

the first slider is provided with a longitudinal through hole and a rotatable locking ring, and a locking ring inner bump is provided on the inner side of the rotatable locking ring; and the second slider is provided with a second claw, and the second claw is adapted to pass through the longitudinal through hole during engagement of the first slider with the second slider.

4. The recapturing method according to claim 3, wherein the first slider is provided with a first claw which is in rotatable engagement with the locking ring inner bump.

5. The recapturing method according to claim 3, wherein an arc-shaped groove is provided on an inner side of the rotatable locking ring or an end surface of the rotatable locking ring close to the first slider, the first slider is provided with a convex portion adapted to the arc-shaped groove, and the convex portion is rotatably engaged with the arc-shaped groove.

6. The recapturing method according to claim 2, wherein the first slider is provided with a first outer protrusion and the second slider is provided a second outer protrusion.

7. The recapturing method according to claim 2, wherein the first slider is a sheath tube piston and the second slider is a net piston.

8. The recapturing method according to claim 2, wherein the first movable barrel is provided with a first inner spiral groove.

9. The recapturing method according to claim 8, wherein the second movable barrel is provided with a second inner spiral groove.

10. The recapturing method according to claim 9, wherein a screw pitch of the first inner spiral groove is greater than a screw pitch of the second inner spiral groove.

* * * * *